US009163236B2

(12) United States Patent
Jessup et al.

(10) Patent No.: US 9,163,236 B2
(45) Date of Patent: Oct. 20, 2015

(54) PHARMACEUTICAL COMPOSITION COMPRISING NANOG SHRNA, AND METHOD OF USING NANOG SHRNA TO TREAT CANCER

(75) Inventors: John Milburn Jessup, Potomac, MD (US); Jingyu Zhang, Rockville, MD (US)

(73) Assignee: The United States of America, as represented by the Secretary, Dept. of Health and Human Services, Washington, DC (US)

( * ) Notice: Subject to any disclaimer, the term of this patent is extended or adjusted under 35 U.S.C. 154(b) by 107 days.

(21) Appl. No.: 13/991,989

(22) PCT Filed: Dec. 6, 2011

(86) PCT No.: PCT/US2011/063451
§ 371 (c)(1),
(2), (4) Date: Aug. 2, 2013

(87) PCT Pub. No.: WO2011/063451
PCT Pub. Date: Aug. 2, 2013

(65) Prior Publication Data
US 2014/0303230 A1    Oct. 9, 2014

Related U.S. Application Data

(60) Provisional application No. 61/420,214, filed on Dec. 6, 2010.

(51) Int. Cl.
| | |
|---|---|
| *C07H 21/02* | (2006.01) |
| *C07H 21/04* | (2006.01) |
| *A61K 48/00* | (2006.01) |
| *C12N 15/63* | (2006.01) |
| *C12N 15/113* | (2010.01) |

(52) U.S. Cl.
CPC .......... *C12N 15/113* (2013.01); *C12N 2310/14* (2013.01); *C12N 2740/16043* (2013.01); *C12N 2740/16045* (2013.01)

(58) Field of Classification Search
CPC ..... A61K 48/00; C12N 15/111; C12N 15/113
See application file for complete search history.

(56) References Cited

FOREIGN PATENT DOCUMENTS

| | | | |
|---|---|---|---|
| WO | WO 2009/126160 A1 | 10/1990 | |
| WO | WO 2006/025802 A1 | 3/2006 | |
| WO | WO 2009/126160 A1 * | 10/2009 | ..................... 514/44 |
| WO | WO 2010/135662 A2 | 11/2010 | |

OTHER PUBLICATIONS

FEBS J. Apr. 2006;273(8):1723-30.*
Cancer Biology & Therapy, vol. 9, issue 4, Feb. 2010.*
Chambers et al; "Functional Expression Cloning of Nanog, a Pluripotency Sustaining Factor in Embryonic Stem Cells"; Cell; vol. 113 Issue 5; May 2003; p. 643-655.
Booth et al.; "Eleven daughters of NANOG"; Genomics; vol. 84 Issue 2; Aug. 2004; p. 229-238.
Zhang et al.; "NANOGP8 is a retrogene expressed in cancers"; The FEBS Journal; vol. 273; Mar. 2006; p. 1723-1730.
Jeter et al.; "Functional Evidence that the Self-Renewal Gene NANOG Regulates Human Tumor Development"; Stem Cells; vol. 27 Issue 5; May 2009; p. 993-1005.
Zbinden et al.; "NANOG regulates glioma stem cells and is essential in vivo acting in a cross-functional network with GLI1 and p53"; The EMBO Journal; vol. 29 Issue 15; Aug. 2010; p. 2659-2674.
Naldini et al.; "In Vivo Gene Delivery and Stable Transduction of Nondividing Cells by a Lentiviral Vector"; Science; vol. 272; Apr. 1996; p. 263-267.
Naldini et al.; "Efficient transfer, integration, and sustained long-term expression of the transgene in adult rat brains injected with a lentviral vector"; Proc. Natl. Acad. Sci. USA; vol. 93; Oct. 1996; p. 11382-11388.
Zufferey et al.; "Multiply attenuated lentiviral vector achieves efficient gene delivery in vivo"; Nature Biotechnology; vol. 15; Sep. 1997; p. 871-875.
Dull et al.; "A Third-Generation Lentivirus Vector with a Conditional Packaging System"; Journal of Virology; vol. 72 No. 11; Nov. 1998; p. 8463-8471.
Miyoshi et al.; "Development of a Self-Inactivating Lentivirus Vector"; Journal of Virology; vol. 72 No. 10; Oct. 1998; p. 8150-8157.
Zufferey et al.; "Self-Inactivating Lentivirus Vector for Safe and Efficient In Vivo Gene Delivery"; Journal of Virology; vol. 72 No. 12; Dec. 1998; p. 9873-9880.
Caplen et al.; "Specific inhibition of gene expression by small double-stranded RNAs in invertebrate and vertebrate systems"; Proc. Natl. Acad. Sci. USA; vol. 98 No. 17; Aug. 2001; p. 9742-9747.
Bernstein et al.; "Role for a bidentate ribonuclease in the initiation step of RNA interference"; Nature; vol. 409; Jan. 2001; p. 363-366.
Boutla et al.; "Short 5'-phosphorylated double-stranded RNAs induce RNA interference in *Drosophila*" Current Biology; vol. 11; Nov. 2001; p. 1776-1780.
Shiau et al.; "Inhibition of experimental lung metastasis by systemic lentiviral delivery of kallistatin"; BMC Cancer; vol. 10 No. 245; 2010; 9 pages.
Deharvengt et al.; "Intratumoral delivery of shRNA targeting cyclin D1 attenuates pancreatic cancer growth"; Cancer Gene Threrapy; vol. 17; 2010; p. 325-333.

(Continued)

*Primary Examiner* — Amy Bowman
(74) *Attorney, Agent, or Firm* — Sheridan Ross P.C.

(57) ABSTRACT

The present description relates to an inhibitory RNA molecule, comprising an oligonucleotide that selectively knocks down expression of either Nanog or a Nanog pseudogene, a vector capable of encoding such inhibitory RNA molecule, pharmaceutical compositions comprising said vector, and methods of treating cancer by administration of said pharmaceutical composition.

24 Claims, 7 Drawing Sheets

(56) References Cited

OTHER PUBLICATIONS

Frade et al.; "Intratumoral gene delivery of anti-cathepsin L single-chain variable fragment by lentiviral vector inhibits tumor progression induced by human melanoma cell"; Cancer Gene Therapy; 2008; vol. 15; p. 591-604.

Duan et al.; "Local delivery of reporter gene to the cochlea does not spread to brain tissue in an animal model"; Acta Octo-Laryngologica; 2010; vol. 130; p. 25-30.

Huang et al.; "Profiling of mismatch discrimination in RNAi enabled rational design of allele-specific siRNAs"; Nucleic Acids Research; 2009; vol. 37 No. 22; p. 7560-7569.

Dykxhoorn et al.; "Determinants of specific RNA interference-mediated silencing of human B-goblin alleles differing by a single nucleotide polymorphism"; PNAS; vol. 103 No. 15; Apr. 2006; p. 5953-5958.

* cited by examiner

SEQUENCE LISTING

```
<160> NUMBER OF SEQ ID NOS: 61

<210> SEQ ID NO 1
<211> LENGTH: 2098
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
attataaatc tagagactcc aggattttaa cgttctgctg gactgagctg gttgcctcat      60
gttattatgc aggcaactca ctttatccca atttcttgat acttttcctt ctggaggtcc     120
tatttctcta acatcttcca gaaaagtctt aaagctgcct taaccttttt tccagtccac     180
ctcttaaatt ttttcctcct cttcctctat actaacatga gtgtggatcc agcttgtccc     240
caaagcttgc cttgctttga agcatccgac tgtaaagaat cttcacctat gcctgtgatt     300
tgtgggcctg aagaaaacta tccatccttg caaatgtctt ctgctgagat gcctcacacg     360
gagactgtct ctcctcttcc ttcctccatg gatctgctta ttcaggacag ccctgattct     420
tccaccagtc ccaaaggcaa acaacccact tctgcagaga agagtgtcgc aaaaaaggaa     480
gacaaggtcc cggtcaagaa acagaagacc agaactgtgt tctcttccac ccagctgtgt     540
gtactcaatg atagatttca gagacagaaa tacctcagcc tccagcagat gcaagaactc     600
tccaacatcc tgaacctcag ctacaaacag gtgaagacct ggttccagaa ccagagaatg     660
aaatctaaga ggtggcagaa aaacaactgg ccgaagaata gcaatggtgt gacgcagaag     720
gcctcagcac ctacctaccc cagcctttac tcttcctacc accagggatg cctggtgaac     780
ccgactggga accttccaat gtggagcaac cagacctgga acaattcaac ctggagcaac     840
cagacccaga acatccagtc ctggagcaac cactcctgga acactcagac ctggtgcacc     900
caatcctgga acaatcaggc ctggaacagt ccttctata actgtggaga ggaatctctg     960
cagtcctgca tgcagttcca gccaaattct cctgccagtg acttggaggc tgccttggaa    1020
gctgctgggg aaggccttaa tgtaatacag cagaccacta ggtattttag tactccacaa    1080
accatggatt tattcctaaa ctactccatg aacatgcaac ctgaagacgt gtgaagatga    1140
gtgaaactga tattactcaa tttcagtctg gacactggct gaatccttcc tctcccctcc    1200
tcccatccct cataggattt ttcttgtttg gaaaccacgt gttctggttt ccatgatgcc    1260
catccagtca atctcatgga gggtggagta tggttggagc ctaatcagcg aggtttcttt    1320 ttttttttttt ttcctattgg atcttcctgg agaaaatact ttttttttttt tttttttga    1380 aacggagtct tgctctgtcg cccaggctgg agtgcagtgg cgcggtcttg gctcactgca    1440
agctccgtct cccgggttca cgccattctc ctgcctcagc ctcccgagca gctgggacta    1500
caggcgcccc ccacctcgcc cggctaatat tttgtatttt tagtagagac ggggtttcac    1560
tgtgttagcc aggatggtct cgatctcctg accttgtgat ccaccgcct cggcctccct    1620
```

| | |
|---|---:|
| aacagctggg atttacaggc gtgagccacc gcgccctgcc tagaaaagac attttaataa | 1680 |
| ccttggctgc cgtctctggc tatagataag tagatctaat actagtttgg atatctttag | 1740 |
| ggtttagaat ctaacctcaa gaataagaaa tacaagtaca aattggtgat gaagatgtat | 1800 |
| tcgtattgtt tgggattggg aggctttgct tatttttaa aaactattga ggtaaagggt | 1860 |
| taagctgtaa catacttaat tgatttctta ccgttttgg ctctgttttg ctatatcccc | 1920 |
| taatttgttg gttgtgctaa tctttgtaga aagaggtctc gtatttgctg catcgtaatg | 1980 |
| acatgagtac tgctttagtt ggtttaagtt caaatgaatg aaacaactat ttttcctta | 2040 |
| gttgatttta ccctgatttc accgagtgtt tcaatgagta aatatacagc ttaaacat | 2098 |

```
<210> SEQ ID NO 2
<211> LENGTH: 2083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
```

| | |
|---|---:|
| ccaggatttt aacgttctgc tggactgagc tggttgcctc atgttattat gcaggcaact | 60 |
| cactttatcc caatttcttg atactttcc ttctggaggt cctatttctc taacatcttc | 120 |
| cagaaaagtc ttaaagctgc cttaaccttt tttccagtcc acctcttaaa ttttttcctc | 180 |
| ctcttcctct atactaacat gagtgtggat ccagcttgtc cccaaagctt gccttgcttt | 240 |
| gaagaatccg actgtaaaga atcttcacct atgcctgtga tttgtgggcc tgaagaaaac | 300 |
| tatccatcct tgcaaatgtc ttctgctgag atgcctcaca cagagactgt ctctcctctt | 360 |
| ccttcctcca tggatctgct tattcaggac agccctgatt cttccaccag tcccaaaggc | 420 |
| aaacaaccca cttctgcaga gaatagtgtc gcaaaaaagg aagacaaggt cccggtcaag | 480 |
| aaacagaaga ccagaactgt gttctcttcc acccagctgt gtgtactcaa tgatagattt | 540 |
| cagagacaga aatacctcag cctccagcag atgcaagaac tctccaacat cctgaacctc | 600 |
| agctacaaac aggtgaagac ctggttccag aaccagagaa tgaaatctaa gaggtggcag | 660 |
| aaaaacaact ggccgaagaa tagcaatggt gtgacgcaga aggcctcagc acctacctac | 720 |
| cccagcctct actcttccta ccaccaggga tgcctggtga cccgactggg aacccttcca | 780 |
| atgtggagca accagacctg gaacaattca acctggagca accagaccca gaacatccag | 840 |
| tcctggagca accactcctg gaacactcag acctggtgca cccaatcctg gaacaatcag | 900 |
| gcctggaaca gtcccttcta taactgtgga gaggaatctc tgcagtcctg catgcacttc | 960 |
| cagccaaatt ctcctgccag tgacttggag gctgccttgg aagctgctgg ggaaggcctt | 1020 |
| aatgtaatac agcagaccac taggtatttt agtactccac aaaccatgga tttattccta | 1080 |
| aactactcca tgaacatgca acctgaagac gtgtgaagat gagtgaaact gatattactc | 1140 |
| aatttcagtc tggacactgg ctgaatcctt cctctcccct cctcccatcc ttcataggat | 1200 |
| ttttcttgtt tggaaaccac gtgttctggt ttccatgatg cccatccagt caatctcatg | 1260 |
| gagggtggag tatggttgga gcctaatcag cgaggtttct ttttttttt ttttttccta | 1320 |
| ttggatcttc ctggagaaaa tacttttttt tttttttttt tttgagacgg agtcttgctc | 1380 |
| tgtcgcccag gctggagtgc agtggcgcgg tcttggctca ctgcaagctc cgtctgccgg | 1440 |
| gttcacgcca ttctcctgcc tcagcctccc gagcagctgg gactacaggc gcccgccacc | 1500 |
| tcgcccggct aatattttgt atttttagta gagacggggt ttcactgtgt tagccaggat | 1560 |

```
ggtctcgatc tcctgacctt gtgatccgcc cgcctcggcc tccctaacag ctgggattta    1620
caggcgtgag ccaccgcgcc ctgcctagaa aagacatttt aataaccttg gctgccgtct    1680
ctggctatag ataagtagat ctaatacgag tttggatatc tttagggttt agaatctaac    1740
ctcaagaata agaaatacaa gtacaaattg gtgatgaaga tgtattcgta ttgtttggga    1800
ttgggaggct ttgcttattt tttaaaaact attgaggtaa agggttaagc tgtaacatac    1860
ttaattgatt tcttaccgtt tttggctctg ttttgctata tccctaatt tgttggttgt     1920 gctaatcttt gtagaaagag gtctcgtatt tgctgcatcg taatgacatg agtactactt    1980
tagttggttt aagttcaaat gaatgaaaca actattttc ctttagttga ttttaccctg     2040
atttcaccga gtgtttcaat gagtaaatat acagcttaaa cat                      2083
```

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

```
gaggcagcag agaccgctgc atgcacttcc agcca                               35
```

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

```
tctgacagga agtggctgga agtgcatgca g                                   31
```

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
cttcctgtca gatggctgga agtgcatgca gttttt                              36
```

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
cgaacagaga gagaccgaaa aactgcatgc acttccagcc a                        41
```

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 7
gaggcagcag agaccgctgc atgcacttcc agccg                                35

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tctgacagga agtggctgga agtgcatgca g                                    31

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cttcctgtca gatggctgga agtgcatgca gttttt                               36

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cgaacagaga gagaccgaaa aactgcatgc acttccagcc g                         41

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gaggcagcag agaccgttgt gatccgcccg cctcg                                35

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tctgacagga agcgaggcgg gcggatcaca a                                    31

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 13
cttcctgtca gacgaggcgg gcggatcaca attttt                               36

<210> SEQ ID NO 14
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cgaacagaga gagaccgaaa aattgtgatc cgcccgcctc g                         41

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gaggcagcag agaccgatct aatacgagtt tggata                               36

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tctgacagga agtatccaaa ctcgtattag at                                   32

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cttcctgtca gatatccaaa ctcgtattag attttt                               37

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cgaacagaga gagaccgaaa aaatctaata cgagtttgga ta                        42

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gaggcagcag agaccgatct aatacgagtt tggatg                           36

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cgaacagaga gagaccgaaa aaatctaata cgagtttgga tg                    42

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gaggcagcag agaccgatga gtactacttt agttg                            35

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tctgacagga agcaactaaa gtagtactca t                                31

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cttcctgtca gacaactaaa gtagtactca tttttt                           36

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cgaacagaga gagaccgaaa aaatgagtac tactttagtt g                     41

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gaggcagcag agaccgaaca aagcacatct tgccagga                                    38

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tctgacagga agtcctggca agatgtgctt tgtt                                        34

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cttcctgtca gatcctggca agatgtgctt tgttttttt                                   39

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cgaacagaga gagaccgaaa aaaacaaagc acatcttgcc agga                             44

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gaggcagcag agaccgaaca aagcacatct tgccaggg                                    38

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tctgacagga agtcctggca agatgtgctt tgtt                                        34

<210> SEQ ID NO 31
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cttcctgtca gatcctggca agatgtgctt tgtttttt    39

<210> SEQ ID NO 32
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cgaacagaga gagaccgaaa aaaacaaagc acatcttgcc aggg    44

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gaggcagcag agaccgctgc atgcagttcc agcca    35

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tctgacagga agtggctgga actgcatgca g    31

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cttcctgtca gatggctgga actgcatgca gttttt    36

<210> SEQ ID NO 36
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cgaacagaga gagaccgaaa aactgcatgc agttccagcc a    41

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gaggcagcag agaccgctgc atgcagttcc agccg                                      35

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tctgacagga agtggctgga actgcatgca g                                          31

<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cttcctgtca gatggctgga actgcatgca gttttt                                     36

<210> SEQ ID NO 40
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cgaacagaga gagaccgaaa aactgcatgc agttccagcc g                               41

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gaggcagcag agaccgtagc gactaaacac atcaa                                      35

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tctgacagga agttgatgtg tttagtcgct a                                          31

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cttcctgtca gattgatgtg tttagtcgct attttt         36

<210> SEQ ID NO 44
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cgaacagaga gagaccgaaa aatagcgact aaacacatca a         41

<210> SEQ ID NO 45
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ccgggctgct aaggacaaca ttgatctcga gatcaatgtt gtccttagca gcttttt         57

<210> SEQ ID NO 46
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ccgggctttg aagcatccga ctgtactcga gtacagtcgg atgcttcaaa gcttttt         57

<210> SEQ ID NO 47
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ccggctgtaa agaatcttca cctatctcga gataggtgaa gattctttac agttttt         57

<210> SEQ ID NO 48
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ccggcctgga acagtccctt ctatactcga gtatagaagg gactgttcca ggttttt         57

<210> SEQ ID NO 49
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 49
ccggcctaaa ctactccatg aacatctcga gatgttcatg gagtagttta ggttttt        57

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ctgcatgcag ttccagcca                                                  19

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tggctggaac tgcatgcag                                                  19

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ctgcatgcag ttccagccg                                                  19

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tggctggaac tgcatgcag                                                  19

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ctgcatgcac ttccagcca                                                  19

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 55
tggctggaag tgcatgcag                                                19

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ctgcatgcac ttccagccg                                                19

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
tggctggaag tgcatgcag                                                19

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys Thr Trp Phe Gln Asn Gln Arg Met
1               5

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Lys Tyr Leu Ser Leu Gln Gln Met Gln Glu Leu Ser Asn Ile Leu Asn
1               5                   10                  15

Leu Ser Tyr Lys Gln
            20

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Lys Glu Asp Lys Val Pro Val Lys Lys
1               5                   10
```

-continued

```
<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Gly Lys Gln Pro Thr Ser Ala Glu Asn Ser Val Ala Lys Lys
1               5                   10                  15
```

PHARMACEUTICAL COMPOSITION COMPRISING NANOG SHRNA, AND METHOD OF USING NANOG SHRNA TO TREAT CANCER

CROSS-REFERENCE TO RELATED APPLICATIONS

This application is the National Stage of International Application No. PCT/US2011/063451 filed Dec. 6, 2011, which claims the benefit of U.S. Provisional Application No. 61/420,214 filed Dec. 6, 2010, the disclosures of which are incorporated herein by reference in their entireties.

TECHNICAL FIELD

The technical field consists of a pharmaceutical composition comprising an oligonucleotide that selectively knocks down expression of either Nanog or a Nanog pseudogene, and a method of treating cancer by administering said pharmaceutical composition to a patient in need thereof.

BACKGROUND

Colorectal carcinoma (CRC) is the second highest cancer-specific mortality in the U.S. population. There remains a need to develop effect therapeutics to prevent and/or treat CRC.

Nanog was identified to be a core embryonic stem cell gene (Chambers et al., 2003, Cell 113:643-55), and was later determined to be associated with a family of eleven pseudogenes on chromosome 12 with the original parent gene (Booth et al., 2004, Genomics 84:229-38). Other members of the family may influence Nanog's function in carcinoma cells, for example by reactivation.

The cancer stem cell hypothesis postulates that a small pluripotent population of cancer cells generates cancer heterogeneity and resistance to chemotherapy and radiation therapy. Three transcription factors, SOX2, OCT4 and Nanog form a core regulatory network that coordinately determines embryonic stem cell self-renewal and differentiation (Zhang et al., 2006, FEBS J 273:1723-30). Cultured cancer cells, as well as xenograft and human primary prostate cancer cells express a functional variant of Nanog, NanogP8, which is enriched in putative cancer stem/progenitor cell populations (Zhang et al.; and Jeter et al. 2009, Stem Cells 27:993-1005). Nanog protein expression is functionally important for tumor development based because knockdown of Nanog expression inhibits growth of xenografts of cancer cells from cancer cell lines Du145 HPCa and LAPC4 (prostate), MCF7 (breast cancer), and Colo320 (colon cancer) (Jeter et al.). NanogP8 is also expressed in human glioblastoma cells (Zbinden et al. 2010, EMBO J 29:2659-74).

The role of Nanog and its pseudogenes in tumorigenesis and progression of metastasis for a number of cancers, including gastric, colorectal (CRC), breast, glioblastoma, cervical cancers is currently unknown.

SUMMARY

One aspect of the description is an inhibitory RNA molecule, comprising an oligonucleotide that knocks down expression of either Nanog or NanogP8. One embodiment is an oligonucleotide that inhibits Nanog but not NanogP8 expression. Another embodiment is an oligonucleotide that inhibits NanogP8 but not Nanog expression. Another embodiment is an oligonucleotide that selectively inhibits another Nanog pseudogene. Another embodiment of the RNA molecule is one in which the oligonucleotide is preferably selected from the group consisting of the shRNA sequences of SEQ ID NOS: 3-44, more preferably selected from the group consisting of SEQ ID NOS: 3, 8, 34, and 37.

Another aspect of the invention is a viral vector, comprising the inhibitory RNA molecule described above. The viral vector preferably is a lentivirus vector. In one embodiment the viral vector is capable of infecting cancer cells. Another embodiment is a lentivirus vector that is an integrating vector. The viral vector preferably is capable of transducing cancer cells. More preferably, the vector is capable of inducing apoptosis of cancer cells. Another embodiment is a viral vector that is capable of inhibiting cancer cell proliferation or inhibiting tumor mass. The viral vector is preferably packaged in a coat protein the specifically binds to CRC cells. The viral vector preferably is capable of inducing spherogenicity of CRC cells in vitro. The viral vector preferably is capable of overexpressing an RNA that inhibits either NanogP8 or Nanog expression. An embodiment of the viral vector is one in which the oligonucleotide is preferably selected from the group consisting of the shRNA sequences of SEQ ID NOS: 3-44, more preferably selected from the group consisting of SEQ ID NOS: 3, 8, 34, and 37. Another embodiment of the invention is one in which the viral vector preferably is a lentivirus vector, more preferably an integrating lentivirus vector. Another embodiment of the invention is one in which the viral vector is preferably produced by a vector transfer cassette and a separate helper plasmid.

Another aspect of the invention is a pharmaceutical composition for treating a cancer, comprising the viral vector described above. One embodiment is a pharmaceutical composition comprising an inhibitory oligonucleotide that is a double stranded RNA molecule. One embodiment of the pharmaceutical composition is one in which the oligonucleotides is a component of a viral vector capable of infecting cancer cells, more preferably colorectal cancer cells. Another embodiment is one in which the viral vector is a lentivirus. Alternatively, the oligonucleotide may be a double stranded siRNA. In either instance, the oligonucleotide is preferably selected from the group consisting of the shRNA sequences of SEQ ID NOS: 3-44, more preferably selected from the group consisting of SEQ ID NOS: 3, 8, 34, and 37.

Another aspect of the invention is a method of treating cancer, comprising administering to a patient in need thereof a pharmaceutical composition that inhibits expression of NanogP8 without substantially changing Nanog function or Nanog without substantially changing NanogP8 function. An embodiment of the method of treating cancer is one which preferably inhibits cancer cells having a malignant phenotype, more preferably cancer cells capable of metastasizing. Another preferred embodiment is a method in which colorectal cancer is treated. Another embodiment is a method of treating cancer by administering to a patient in need thereof an effective amount of the pharmaceutical compositions described above.

DETAILED DESCRIPTION OF ILLUSTRATIVE EMBODIMENTS

Figure 1:
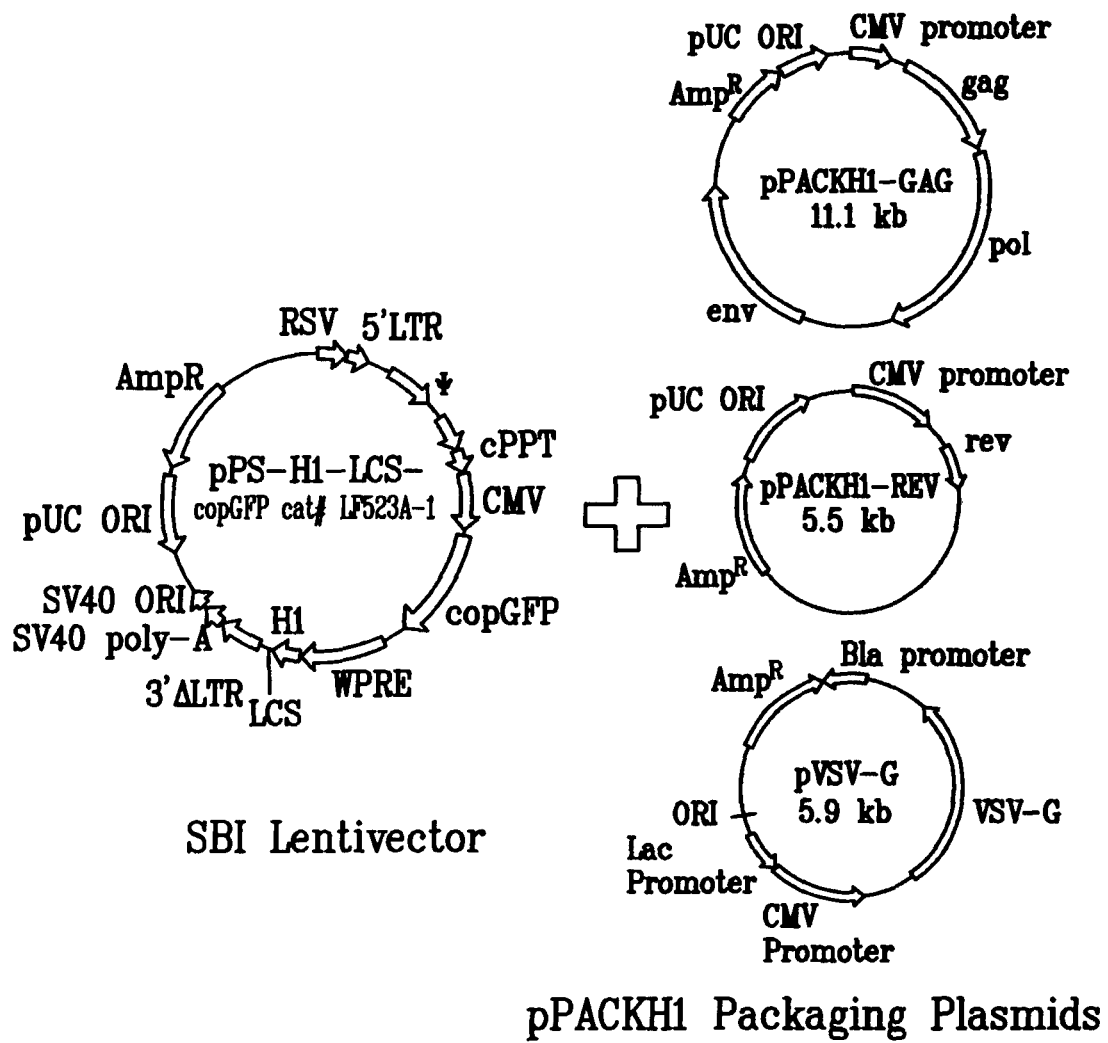
FIG. 1 shows shRNA vector, pPS-H1-LCS-GFP, and packaging plasmids, pVSV-G and pPACK-GAG/REV. The SBI Clone-it enzyme free system was used according to the manufacturer's protocol to assemble the shRNAs described herein. The shRNAs were cloned into the Ligase Cloning Site (LCS) in the SBI lentivector and sequences confirmed by sequencing. HEK293TN cells were used for packaging according to the protocol from manufacturer.

What is described herein is an allele-specific shRNA knocks down expression of NanogP8 while not interfering with expression of Nanog.

Nanog mRNA has the following structure, based on a cDNA sequence (SEQ ID NO:1)

```
   1 attataaatc tagagactcc aggattttaa cgttctgctg gactgagctg gttgcctcat
  61 gttattatgc aggcaactca ctttatccca atttcttgat acttttcctt ctggaggtcc
 121 tatttctcta acatcttcca gaaaagtctt aaagctgcct taaccttttt tccagtccac
 181 ctcttaaatt ttttcctcct cttcctctat actaacatga gtgtggatcc agcttgtccc
 241 caaagcttgc cttgctttga agcatccgac tgtaaagaat cttcacctat gcctgtgatt
 301 tgtgggcctg aagaaaacta tccatccttg caaatgtctt ctgctgagat gcctcacacg
 361 gagactgtct ctcctcttcc ttcctccatg gatctgctta ttcaggacag ccctgattct
 421 tccaccagtc ccaaaggcaa acaacccact tctgcagaga agagtgtcgc aaaaaaggaa
 481 gacaaggtcc cggtcaagaa acagaagacc agaactgtgt tctcttccac ccagctgtgt
 541 gtactcaatg atagatttca gagacagaaa tacctcagcc tccagcagat gcaagaactc
 601 tccaacatcc tgaacctcag ctacaaacag gtgaagacct ggttccagaa ccagagaatg
 661 aaatctaaga ggtggcagaa aaacaactgg ccgaagaata gcaatggtgt gacgcagaag
 721 gcctcagcac ctacctaccc cagcctttac tcttcctacc accagggatg cctggtgaac
 781 ccgactggga accttccaat gtggagcaac caatcctgga caattcaac ctggagcaac
 841 cagacccaga acatccagtc ctggagcaac cactcctgga cactcagac ctggtgcacc
 901 caatcctgga acaatcaggc ctggaacagt cccttctata actgtggaga ggaatctctg
 961 cagtcctgca tgcagttcca gccaaattct cctgccagtg acttggaggc tgccttggaa
1021 gctgctgggg aaggccttaa tgtaatacag cagaccacta ggtattttag tactccacaa
1081 accatggatt tattcctaaa ctactccatg aacatgcaac ctgaagacgt gtgaagatga
1141 gtgaaactga tattactcaa tttcagtctg gacactggct gaatccttcc tctcccctcc
```

```
1201 tcccatccct cataggattt ttcttgtttg gaaaccacgt gttctggttt ccatgatgcc 1261 catccagtca atctcatgga gggtggagta tggttggagc ctaatcagcg aggtttcttt 1321 tttttttttt ttcctattgg atcttcctgg agaaaatact tttttttttt ttttttttga 1381 aacggagtct tgctctgtcg cccaggctgg agtgcagtgg cgcggtcttg gctcactgca 1441 agctccgtct cccgggttca cgccattctc ctgcctcagc ctcccgagca gctgggacta 1501 caggcgcccg ccacctcgcc cggctaatat tttgtatttt tagtagagac ggggtttcac 1561 tgtgttagcc aggatggtct cgatctcctg accttgtgat ccacccgcct cggcctccct 1621 aacagctggg atttacaggc gtgagccacc gcgcctgcc tagaaaagac attttaataa 1681 ccttggctgc cgtctctggc tatagataag tagatctaat actagtttgg atatctttag 1741 ggtttagaat ctaacctcaa gaataagaaa tacaagtaca aattggtgat gaagatgtat 1801 tcgtattgtt tgggattggg aggctttgct tattttttaa aaactattga ggtaaagggt 1861 taagctgtaa catacttaat tgatttctta ccgttttttgg ctctgttttg ctatatcccc 1921 taatttgttg gttgtgctaa tctttgtaga aagaggtctc gtatttgctg catcgtaatg 1981 acatgagtac tgctttagtt ggtttaagtt caaatgaatg aaacaactat ttttccttta 2041 gttgattta ccctgatttc accgagtgtt tcaatgagta aatatacagc ttaaacat
```

The sequence of NanogP8, based on the cDNA structure is as follows (SEQ ID NO:2):

```
  1 ccaggatttt aacgttctgc tggactgagc tggttgcctc atgttattat gcaggcaact 61 cactttatcc caatttcttg atacttttcc ttctggaggt cctatttctc taacatcttc 121 cagaaaagtc ttaaagctgc cttaaccttt tttccagtcc acctcttaaa ttttttcctc 181 ctcttcctct atactaacat gagtgtggat ccagcttgtc cccaaagctt gccttgcttt 241 gaagaatccg actgtaaaga atcttcacct atgcctgtga tttgtgggcc tgaagaaaac 301 tatccatcct tgcaaatgtc ttctgctgag atgcctcaca cagagactgt ctctcctctt 361 ccttcctcca tggatctgct tattcaggac agccctgatt cttccaccag tcccaaaggc 421 aaacaaccca cttctgcaga gaatagtgtc gcaaaaaagg aagacaaggt cccggtcaag 481 aaacagaaga ccagaactgt gttctcttcc acccagctgt gtgtactcaa tgatagattt 541 cagagacaga aatacctcag cctccagcag atgcaagaac tctccaacat cctgaacctc 601 agctacaaac aggtgaagac ctggttccag aaccagagaa tgaaatctaa gaggtggcag 661 aaaaacaact ggccgaagaa tagcaatggt gtgacgcaga aggcctcagc acctacctac 721 cccagcctct actcttccta ccaccaggga tgcctggtga cccgactgg gaaccttcca 781 atgtggagca accagacctg gaacaattca acctggagca accagaccca gaacatccag 841 tcctggagca accactcctg gaacactcag acctggtgca cccaatcctg gaacaatcag 901 gcctggaaca gtcccttcta taactgtgga gaggaatctc tgcagtcctg catgcacttc 961 cagccaaatt ctcctgccag tgacttggag gctgccttgg aagctgctgg ggaaggcctt 1021 aatgtaatac agcagaccac taggtatttt agtactccac aaaccatgga tttattccta 1081 aactactcca tgaacatgca acctgaagac gtgtgaagat gagtgaaact gatattactc 1141 aatttcagtc tggacactgg ctgaatcctt cctctcccct cctcccatcc ttcataggat 1201 ttttcttgtt tggaaaccac gtgttctggt ttccatgatg cccatccagt caatctcatg 1261 gagggtggag tatggttgga gcctaatcag cgaggtttct tttttttttt tttttttccta 1321 ttggatcttc ctggagaaaa tacttttttt tttttttttt tttgagacgg agtcttgctc
```

```
                         -continued
1381 tgtcgcccag gctggagtgc agtggcgcgg tcttggctca ctgcaagctc cgtctgccgg 1441 gttcacgcca ttctcctgcc tcagcctccc gagcagctgg gactacaggc gcccgccacc 1501 tcgcccggct aatattttgt attttagta gagacggggt ttcactgtgt tagccaggat 1561 ggtctcgatc tcctgacctt gtgatccgcc cgcctcggcc tccctaacag ctgggattta 1621 caggcgtgag ccaccgcgcc ctgcctagaa aagacatttt aataaccttg gctgccgtct 1681 ctggctatag ataagtagat ctaatacgag tttggatatc tttagggttt agaatctaac 1741 ctcaagaata agaaatacaa gtacaaattg gtgatgaaga tgtattcgta ttgtttggga 1801 ttgggaggct ttgcttattt tttaaaaact attgaggtaa agggttaagc tgtaacatac 1861 ttaattgatt tcttaccgtt tttggctctg ttttgctata tcccctaatt tgttggttgt 1921 gctaatcttt gtagaaagag gtctcgtatt tgctgcatcg taatgacatg agtactactt 1981 tagttggttt aagttcaaat gaatgaaaca actatttttc ctttagttga ttttaccctg 2041 atttcaccga gtgtttcaat gagtaaatat acagcttaaa cat
```

Using an algorithm, an oligonucleotide was selected in which shRNA sequences are selected from the group consisting of SEQ ID NOS:3-44, preferably selected from the group consisting of SEQ ID NOS: 3, 8, 34, and 37 (sec Table 3, below).

The RNA can be single stranded, including antisense or shRNA. The RNA can be double stranded, including siRNA. In every instance, the RNA must be capable of hybridizing with NanogP8 mRNA having the sequence corresponding to cDNA of SEQ ID NO:2.

Lentiviral shRNA Vector Preparation

The RNA can be a component of a viral vector, or a shRNA encoded by a viral vector. In either instance, the viral vector comprises an oligonucleotide that inhibits expression of NanogP8 while not interfering with expression of Nanog, or encodes a shRNA having such capability.

The sequence of the oligonucleotide is preferably selected from the group consisting of the shRNA sequences of SEQ ID NOS:3-44, more preferably selected from the group consisting of SEQ ID NOS: 3, 8, 34, and 37.

The viral vector preferably is a lentivirus vector, more preferably an integrating lentivirus vector. The ability of the vector to infect cancer cells can be measured with a variety of cell lines, including primary cultures of tumor cells. The ability of the vector to transduce cancer cells can readily be measured by measuring nuclear DNA integration.

A variety of biological functions can be measured to demonstrate the efficacy of the virus in vitro and in vivo using animal models, including the ability to induce apoptosis of cancer cells, the ability to inhibit cancer cell proliferation. Separately, the ability of the vector to inhibit tumor mass can be measured, most easily where the tumor mass is a xenograft. It may be important to measure the ability of the viral vector to induce spherogenicity in vitro, and to inhibit formation of malignant tumor cells.

Lentiviral Produced shRNA

A lentiviral vector is infectious lentiviral particle. An infectious lentiviral particle is capable of invading a target host cell, include an envelope and exhibit one or more characteristics of a lentivirus, e.g., containing a lentiviral virion including one or more of the gag structural polypeptides p7, p24 or p17, containing a lentiviral envelope including one or more of the env encoded glycoproteins p41, p120 or p160, containing a genome including one or more lentivirus cis-acting sequences functioning in replication, proviral integration or transcription, containing a genome encoding a lentiviral protease, reverse transcriptase or integrase, or containing a genome encoding regulatory activities such as Tat or Rev.

A lentiviral vector can exhibit some or all of the natural functions of a lentivirus. A lentiviral vector also can exhibit functions additional to, or different from, a naturally occurring lentivirus. For example, a lentiviral vector can be modified to augment or reduce a lentivirus characteristic or to exhibit characteristics of host cells or heterologous cells. Modifications can include, for example, conferring additional or alternative host cell specificity such as by pseudotyping; augmenting or modulating infectivity by, for example, modifying the binding or fusion functions of an envelope polypeptide; incorporating heterologous, chimeric or multifunctional polypeptides or other membrane components into the envelope; or conferring expression of heterologous genes onto a lentiviral vector genome. Therefore, depending of the design and incorporation of lentivirus constituent components, a lentiviral vector can be, for example, replication-competent, replication incompetent or contain some or all cis elements or trans-acting factors. As such, the term is intended to include enveloped retroviral like particles that derive from or contain at least one functional characteristic of a lentivirus and which is capable of invading a target host cell.

A lentiviral vector genome is a nucleic acid that encodes a lentiviral cis nucleic acid sequence required for genome packaging. A lentiviral vector genome also can encode other cis nucleic acid sequences beneficial for gene delivery, including for example, cis sequences required for reverse transcription, proviral integration or genome transcription. A lentiviral vector genome performs transduction functions of a lentiviral vector. As such, the exact makeup of a vector genome will depend on the genetic material desired to be introduced into a target cell. Therefore, a vector genome can encode, for example, additional polypeptides or functions other than that required for packaging, reverse transcription, integration, or transcription. Such functions generally include coding for cis elements required for expression of a nucleic acid of interest. The lentiviral cis sequences or elements can be derived from a lentivirus genome, a lentiviral vector genome or other virus or vector genome so long as the lentiviral vector genome can be packaged by a lentiviral vector and introduced into a target cell.

A nucleic acid vector is any nucleic acid that functions to carry, harbor or express a nucleic acid of interest. Nucleic acid vectors can have specialized functions such as expression, packaging, pseudotyping, transduction or sequencing, for example. Nucleic acid vectors also can have, for example, manipulatory functions such as a cloning or shuttle vector. The structure of the vector can include any desired form that is feasible to make and desirable for a particular use. Such forms include, for example, circular forms such as plasmids and phagemids, as well as linear or branched forms. A nucleic acid vector can be composed of, for example, DNA or RNA, as well as contain partially or fully, nucleotide derivatives, analogs and mimetics. Such nucleic acid vectors can be obtained from natural sources, produced recombinantly or chemically synthesized.

A packaging construct is a nucleic acid vector that encodes retroviral structural polypeptides sufficient for vector production. When used in reference to a lentiviral nucleic acid vector, the term is intended to refer to lentiviral structural polypeptides sufficient for lentiviral vector production. A lentiviral packaging construct can additionally contain other polypeptides that function in trans to facilitate, augment or supplement the efficiency of vector production or the functional characteristics of the vector particle. Structural polypeptides that function in trans for vector production included, for example, lentiviral polypeptides p6, p7, p17 and p24, which are encoded by gag and reverse transcriptase, protease and integrase, which are encoded by pol. Other trans-acting factors that can function in vector production include, for example, the polypeptides encoded by rev and tat. A packaging construct can be designed to express some or all of such trans-acting factors stably or transiently. Additionally, it should be understood that the term is intended to include construct designs that separate or split the expression of trans-acting factors, or components thereof, onto two or more nucleic acid vectors. Accordingly, a packaging construct can include multiple different nucleic acid vectors which together encode structural polypeptides sufficient for retroviral vector production.

A targeting polypeptide is a polypeptide that contains a binding partner to a molecule expressed on the surface of a targeted cell or tissue, or to a molecule that is otherwise accessible to the vector particle. Expression of a binding partner on a lentiviral vector of the invention allows the vector to be directed to, bind and attach to a predetermined target cell or tissue type. A targeting polypeptide can consist of, or include, any molecule that exhibits binding affinity forward a cognate binding partner. Therefore, targeting polypeptides can include, for example, ligands, receptors, co-receptors, counter-ligands, counter-receptors, antigens and epitopes, as well as other affinity binders well known to those skilled in the art.

A ligand is a molecule that exhibits selective binding affinity for another molecule. Therefore, the term refers to one component of a bi- or multi-component affinity binding reaction. As one constituent of two or more interacting molecular binding species the term is intended to be neutral with reference to orientation. Therefore, a ligand can refer to all types of affinity ligands well known to those skilled in the art including, for example, ligands, haptens, counter-ligands, receptors and counter-receptors. Ligands include a wide range of molecular species well known to those skilled in the art including, for example, polypeptides, nucleic acid and other macromolecules as well as small inorganic or organic molecules.

A receptor is a molecule that exhibits selective binding affinity for another molecule. A receptor can refer to all types of affinity binding molecules well known to those skilled in the art including, for example, receptors, counter-receptors, counter-ligands, ligands and haptens. Where both or all components of a receptor binding reaction are referred to herein, reference may be made to one component as a receptor and to the cognate component counter-receptor or ligand. However, it is understood that a receptor can be referred to equally as either a receptor or a ligand or by any other nomenclature well known to those skilled in the art which designates a pair or complex of affinity binding components. Binding of a receptor to its partner can be, for example, through non-covalent or covalent interactions and can include, for example, binding affinity to polypeptides, nucleic acid, other macromolecules and small molecules. Receptors include a wide range of molecular species well known to those skilled in the art including, for example, polypeptides, nucleic acid and other macromolecules as well as small inorganic or organic molecules.

A lentivirus is an icosahedral enveloped virus having a diploid RNA genome that becomes integrated into the host chromosome as a proviral DNA for genome replication. The lentiviral genome contains gag, pol and env genes which encode the structural polypeptides of the virion (p17, p24, p7 and p6); the viral enzymes protease, reverse transcriptase and integrase, and the envelope glycoproteins (gp120 and gp41), respectively. The lentiviral genome also encodes two regulatory polypeptides (Tat and Rev) and four accessory polypeptides that play a role in virulence (Vif, Vpu, Vpr and Nef). Lentiviruses also have the ability to efficiently infect and transduce proliferating cells. Despite the pathogenesis associated with lentiviruses, it is well known to those skilled in the art that the undesirable properties of lentiviruses can be recombinantly separated so that its beneficial characteristics can be harnessed as a delivery vehicle for therapeutic or diagnostic genes. Therefore, lentiviral-based vectors can be produced that are safe, replication-defective and self-inactivating while still maintaining the beneficial ability to transduce non-dividing cells and integrate into the host chromosome for stable expression. A description of the various different modalities of lentiviral vector and packaging systems for vector assembly and gene delivery can be found in, for example, in Naldini et al., *Science* 272:263-267 (1996); Naldini et al, *Proc. Natl. Acad. Sci. USA* 93:11382-11388 (1996); Zufferey et al, *Nature Bio.* 15:871-875 (1997); Dull et al. *J. Virol.* 72:4638471 (1998); Miyoshi et al, *J. Virol.* 72:8150-8157 (1998), and Zufferey et al., *J. Virol.* 72:9873-9880 (1998). Desirable targeting specificities can include highly specific lentiviral targeting vectors as well as broad spectrum targeting vectors. For example, highly specific, or mono-specific, lentiviral targeting vectors of the invention can be generated, for example, by using a heterologous targeting polypeptide that has a corresponding binding partner specific to a particular cell type or tissue. In contrast, broad spectrum targeting vectors can be generated by using a heterologous targeting polypeptide that has a cognate binding partner on multiple different cell types or tissues or by using multiple different heterologous targeting polypeptides that have specificities to different cell types or tissues. Being able to engineer a single specificity to a unique target cell marker, multiple specificities unique to different target cells or a single specificity to a ubiquitous marker provides the lentiviral vectors of the invention with flexible and versatile targeting capabilities because they can be tailored for many different targeting and delivery applications.

Highly specific lentiviral targeting vectors can be useful as delivery vehicles for therapeutic or diagnostic nucleic acids or other compounds when, for example, it is desirable to target a particular tissue, a particular class of cell types, a particular cell type or one or more particular subtypes of any of these categories. Such specific lentiviral vectors can be generated with a heterologous targeting polypeptide that exhibit binding affinity to a unique cognate binding partner on the targeted tissue, class, cell type or subtype for the delivery of a therapeutic or diagnostic molecule. Broad spectrum or ubiquitous targeting vectors can be useful as delivery vehicles for therapeutic molecules when, for example, pathogenesis or the causative agent is pleiotropic in nature. Ubiquitous targeting vectors also are useful as delivery vehicles for diagnostic molecules to, for example, identify regions of pathogenesis or to ascertain the cause or symptoms of an aberrant condition. As described further below, the therapeutic or diagnostic nucleic acids or compounds include, for example, an encoding nucleic acid such as a transgene, that when expressed in the targeted cell or tissue produces a polypeptide having the desired therapeutic or diagnostic activity.

Engineering a predetermined binding specificity into the vector can be achieved by incorporating into a vector envelope a targeting polypeptide having a desired binding specificity. Because a lentivirus is an enveloped virus, a targeting polypeptide can be incorporated by, for example, normal cellular processes for transmembrane insertion, or for membrane attachment or anchoring, of polypeptides, lipids and other macromolecules. For example, a targeting polypeptide can contain a transmembrane domain or a membrane attachment domain that incorporates into, or is capable of incorporating into, a lentiviral vector envelope. Alternatively, a targeting polypeptide can contain a membrane anchoring domain that signals attachment to, for example, a lipid anchor. Nucleic acids encoding a particular targeting polypeptide can be generated by recombinant methods or chemical synthesis and then expressed in a vector packaging system for automatic incorporation into a lentiviral vector envelope. Alternatively, a particular targeting polypeptide can be produced in vitro or chemically synthesized and then incorporated into a vector envelope using a cell-free system. Therefore, the targeting polypeptides of the invention include integral membrane polypeptides, peripheral membrane polypeptides as well as those polypeptides anchored by other non-polypeptide molecules or macromolecules.

Other methods known to those skilled in the art also can be used for incorporation or attachment of a targeting polypeptide into a lentiviral vector of the invention. Such other methods include, for example, the noncovalent association of a targeting polypeptide with a envelope associated polypeptide, lipid, carbohydrate or other molecule, or chemical conjugation. Therefore, incorporation can be accomplished using a variety of methods well known to those skilled in the art.

A targeting polypeptide can be, in whole or in part, heterologous or homologous to a lentiviral polypeptide so long as it can incorporate, or be made to incorporate, into a vector envelope of the invention. For example, a heterologous targeting polypeptide can be derived from a species other than lentivirus or derived from a molecule different from the lentivirus gp160 or gp120 envelope polypeptides. Where a targeting polypeptide is heterologous, it is sufficient for at least one portion of the targeting polypeptide to be derived from a non-lentiviral species or non-lentiviral envelope polypeptide.

Targeting polypeptides useful in the lentiviral vectors of the invention include those polypeptides that exhibit binding affinity toward a cognate binding partner on a target of interest. A targeting polypeptide can include, for example, an affinity ligand, a receptor, an antibody, counter-ligand or counter-receptor so long as it exhibits binding affinity toward a cognate binding partner. Specific examples of targeting polypeptides include, for example, transferrin, an apolipoprotein, Rabies G glycoprotein and lentivirus gp120.

RNA interference (RNAi) is mediated by double stranded RNA (dsRNA) molecules that have sequence-specific homology to their target nucleic acid sequences (Caplen, N. J., et al, Proc. Natl. Acad. Sci. USA 98:9742-9747 (2001)). Biochemical studies in *Drosophila* cell-free lysates indicate that, in certain embodiments of the present invention, the mediators of RNA-dependent gene silencing are 21-25 nucleotide "small interfering" RNA duplexes (siRNAs). The siRNAs are derived from the processing of dsRNA by an RNase enzyme known as Dicer (Bernstein, E., et al, Nature 409:363366 (2001)). siRNA duplex products are recruited into a multi-protein siRNA complex termed RISC (RNA Induced Silencing Complex). A RISC is then believed to be guided to a target nucleic acid (suitably mRNA), where the siRNA duplex interacts in a sequence-specific way to mediate cleavage in a catalytic fashion (Bernstein, E., et al, Nature 409: 363-366 (2001); Boutla, A., et al, Curr. Biol. 11:1776-1780 (2001)). Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 0 to about 50 nucleotides (nt). In examples of nonlimiting embodiments, siRNAs can comprise about 5 to about 40 nt, about 5 to about 30 nt, about 10 to about 30 nt, about 15 to about 25 nt, or about 20-25 nucleotides.

An RNAi is an at least partly double-stranded RNA having a structure characteristic of molecules that are known in the art to mediate inhibition of gene expression through an RNAi mechanism or an RNA strand comprising at least partially complementary portions that hybridize to one another to form such a structure. When an RNA comprises complementary regions that hybridize with each other, the RNA will be said to self-hybridize. An RNAi agent includes a portion that is substantially complementary to a target gene. An RNAi agent, optionally includes one or more nucleotide analogs or modifications. One of ordinary skill in the art will recognize that RNAi agents that are synthesized in vitro can include ribonucleotides, deoxyribonucleotides, nucleotide analogs, modified nucleotides or backbones, etc., whereas RNAi agents synthesized intracellularly, e.g., encoded by DNA templates, typically consist of RNA, which may be modified following transcription. Of particular interest herein are short RNAi agents, i.e., RNAi agents consisting of one or more strands that hybridize or self-hybridize to form a structure that comprises a duplex portion between about 15-29 nucleotides in length, optionally having one or more mismatched or unpaired nucleotides within the duplex. RNAi agents include short interfering RNAs (siRNAs), short hairpin RNAs (shRNAs), and other RNA species that can be processed intracellularly to produce shRNAs including, but not limited to, RNA species identical to a naturally occurring miRNA precursor or a designed precursor of an miRNA-like RNA.

The term "short, interfering RNA" (siRNA) refers to a nucleic acid that includes a double-stranded portion between about 15-29 nucleotides in length and optionally further comprises a single-stranded overhang {e.g., 1-6 nucleotides in length) on either or both strands. The double-stranded portion is typically between 17-21 nucleotides in length, e.g., 19 nucleotides in length. The overhangs are typically present on the 3' end of each strand, are usually 2 nucleotides long, and are composed of DNA or nucleotide analogs. An siRNA may be formed from two RNA strands that hybridize together, or may alternatively be generated from a longer double-stranded RNA or from a single RNA strand that includes a self-hybridizing portion, such as a short hairpin RNA. One of ordinary skill in the art will appreciate that one or more, mismatches or unpaired nucleotides can be present in the duplex formed by the two siRNA strands. One strand of an siRNA (the "antisense" or "guide" strand) includes a portion that hybridizes with a target nucleic acid, e.g., an mRNA transcript. Typically the antisense strand is perfectly complementary to the target over about 15-29 nucleotides, typically between 17-21 nucleotides, e.g., 19 nucleotides, meaning that the siRNA hybridizes to the target transcript without a single mismatch over this length. However, one of ordinary skill in the art will appreciate that one or more mismatches or unpaired nucleotides may be present in a duplex formed between the siRNA strand and the target transcript.

A short hairpin RNA (shRNA) is a nucleic acid molecule comprising at least two complementary portions hybridized or capable of hybridizing to form a duplex structure sufficiently long to mediate RNAi (typically between 15-29 nucleotides in length), and at least one single-stranded portion, typically between approximately 1 and 10 nucleotides in length that forms a loop connecting the ends of the two sequences that form the duplex. The structure may further comprise an overhang. The duplex formed by hybridization of self-complementary portions of the shRNA has similar properties to those of siRNAs and, as described below, shRNAs are processed into siRNAs by the conserved cellular RNAi machinery. Thus shRNAs are precursors of siRNAs and are similarly capable of inhibiting expression of a target transcript. As is the case for siRNA, an shRNA includes a portion that hybridizes with a target nucleic acid, e.g., an mRNA transcript and is usually the perfectly complementary to the target over about 15-29 nucleotides, typically between 17-21 nucleotides, e.g., 19 nucleotides. However, one of ordinary skill in the art will appreciate that one or more mismatches or unpaired nucleotides may be present in a duplex formed between the shRNA strand and the target transcript.

An RNAi agent is considered to be "targeted" to a transcript and to the gene that encodes the transcript if (1) the RNAi agent comprises a portion, e.g., a strand, that is at least approximately 80%, approximately 85%, approximately 90%, approximately 91%, approximately 92%, approximately 93%, approximately 94%, approximately 95%, approximately 96%, approximately 97%, approximately 98%, approximately 99%, or approximately 100% complementary to the transcript over a region about 15-29 nucleotides in length, e.g., a region at least approximately 15, approximately 17, approximately 18, or approximately 19 nucleotides in length; and/or (2) the Tm of a duplex formed by a stretch of 15 nucleotides of one strand of the RNAi agent and a 15 nucleotide portion of the transcript, under conditions (excluding temperature) typically found within the cytoplasm or nucleus of mammalian cells is no more than approximately 15° C. lower or no more than approximately 10° C. lower, than the Tm of a duplex that would be formed by the same 15 nucleotides of the RNAi agent and its exact complement; and/or (3) the stability of the transcript is reduced in the presence of the RNAi agent as compared with its absence. An RNAi agent targeted to a transcript is also considered targeted to the gene that encodes and directs synthesis of the transcript. A target region is a region of a target transcript that hybridizes with an antisense strand of an RNAi agent. A target transcript is any RNA that is a target for inhibition by RNA interference.

Lentivectors with the Ligase-free Clone-IT™ system in which shRNAs are assembled under the control of the H1 promoter as well as a GFP protein (copGFP) under control of the CMV promoter may be used to produce specific shRNA. The lentivector is created as vector particles that are pseudotyped with the VSV-G envelope protein by transient transfection of 293T cells with co-transfection of three separate packaging plasmids as diagrammed below: SBI's Expression lentivectors together with the pPACK packaging plasmids are third-generation lentiviral expression systems.

This four plasmid co-transfection system is designed to increase the safety of the HIV-based lentivectors by decreasing the chance of recombination for the potential generation of replication-competent lentivirus (RCL) during production.

The RSV promoter upstream of 5' LTR in the lentivector allows efficient Tat-independent production of viral RNA, reducing the number of genes from HIV-1 that are used in this system that also has eliminated tat.

Number of lentiviral genes necessary for packaging, replication and transduction is reduced to three (gag, pol, rev), and the corresponding proteins are expressed from different plasmids lacking packaging signals. None of the HIV-1 genes (gag, pol, rev) are present in the packaged viral genome, as they are expressed from packaging plasmids lacking a packaging signal.

Pseudoviral particles will carry two copies of the shRNA construct. In addition, a deletion in the enhancer of the U3 region of 3' LTR in the vector transfer plasmid promotes self-inactivation of the lentiviral construct after transduction and integration into genomic DNA of the target cells and is thought to reduce potential insertional mutagenesis following transduction of the cells of interest.

RNA Delivery by Liposome-Nucleic Acid Particles

A lipid particle is a lipid formulation that can be used to deliver an active agent or therapeutic agent, such as a nucleic acid (e.g., an interfering RNA), to a target site of interest (e.g., cell, tissue, organ, and the like). The lipid particle may be a nucleic acid-lipid particle, which is typically formed from a cationic lipid, a non-cationic lipid, and optionally a conjugated lipid that prevents aggregation of the particle. The nucleic acid may be encapsulated in the lipid portion of the particle, thereby protecting it from enzymatic degradation.

A stable nucleic acid-lipid particle a particle made from lipids (e.g., a cationic lipid, a non-cationic lipid, and optionally a conjugated lipid that prevents aggregation of the particle), wherein the interfering RNA is fully encapsulated within the lipid.

The lipid particles typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant in aqueous solution to degradation with a nuclease A lipid particle provides an interfering RNA with full encapsulation, partial encapsulation, or both. In a preferred embodiment, the nucleic acid is fully encapsulated in the lipid particle to form a nucleic acid-lipid particle.

A conjugated lipid inhibits aggregation of lipid particles, including, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides, cationic PEG lipids, polyoxazoline (POZ)-lipid conjugates (e.g., POZ-DAA conjugates; polyamide oligomers (e.g., ATTA-lipid conjugates), and mixtures thereof. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain preferred embodiments, non-ester containing linker moieties, such as amides or carbamates, are used.

An amphipathic lipid has a hydrophobic portion that orients into a hydrophobic phase, and a hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and (3-acyloxyacids, are also within the group designated as amphipathic lipids. Additionally, the amphipathic lipids described above can be mixed with other lipids including triglycerides and sterols.

A neutral lipid exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

A non-cationic lipid may be any amphipathic lipid as well as any other neutral lipid or anionic lipid.

An anionic lipid is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleoylphosphatidylglycerol (POPG), and other anionic modifying groups joined to neutral lipids.

A hydrophobic lipid has apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane. The nucleic acid-lipid particle comprises: (a) a nucleic acid (e.g., an interfering RNA); (b) a cationic lipid comprising from about 50 mol % to about 65 mol % of the total lipid present in the particle; (c) a non-cationic lipid comprising from about 25 mol % to about 45 mol % of the total lipid present in the particle; and (d) a conjugated lipid that inhibits aggregation of particles comprising from about 5 mol % to about 10 mol % of the total lipid present in the particle.

The nucleic acid-lipid particle comprises: (a) a nucleic acid (e.g., an interfering RNA); (b) a cationic lipid comprising from about 50 mol % to about 60 mol % of the total lipid present in the particle; (c) a mixture of a phospholipid and cholesterol or a derivative thereof comprising from about 35 mol % to about 45 mol % of the total lipid present in the particle; and (d) a PEG-lipid conjugate comprising from about 5 mol % to about 10 mol % of the total lipid present in the particle.

In certain other embodiments, the nucleic acid-lipid particle comprises: (a) a nucleic acid (e.g., an interfering RNA); (b) a cationic lipid comprising from about 55 mol % to about 65 mol % of the total lipid present in the particle; (c) cholesterol or a derivative thereof comprising from about 30 mol % to about 40 mol % of the total lipid present in the particle; and (d) a PEG-lipid conjugate comprising from about 5 mol % to about 10 mol % of the total lipid present in the particle.

Monitoring of the Transduced Cells

Cells transduced with the lentiviral vectors produced using the SBI's system is monitored based on the expression of the green fluorescent protein. Monitoring is performed using quantitative PCR methods based on the detection of the genetic marker Gtag that is a 227 bp non-coding sequence derived from EGFP. Since Gtag is derived from EGFP, the cells transduced with the SBI's LVs are monitored by qPRC using the Gtag primers set and probe.

Generation of Replication Competent Lentivirus (RCL) Cell Lines

The LV shRNA will be incubated with human CRC cell lines that have been found to be free of pathogens including HIV. These include Clone A and CX-1 human CRC lines; LEC-009 and LEC-011 cell lines; and a third cell line, LS 174T (ATCC); KM-12c and HCC 2998 (NCI-60 repository through the Developmental Therapeutics Program at the NCI).

Animals

The mice are NOD/SCID mice that are generally considered a non-permissive host. However, it is clear that local (Matsumoto et al., 2010, BMC Gastroenterology 10:44) or systemic (Shiau et al., 2010, BMC Cancer 10:245) delivery of LV delivered genes or inhibitory RNA can transduce mouse cells with the vector-delivered gene or product. However, since the mice lack HIV LV components (gag, pol and env for instance), they will not be able to support recombination events leading to subsequent viral replication within the mice. Mice will be injected with LV either intratumorally or systemically via tail vein injection. Local treatment causes transduction of target genes locally but does not cause transduction in distant tissues. In contrast, systemic injection of VSV-G vector particles via the tail vein in another report does lead to transduction in liver, lung and other organs (Shiau et al.). Several investigators have demonstrated that intratumoral injection of xenografts in mice with lentiviral shRNA to different genes (Deharvengt et al., 2010, Cancer Gene Ther. 17:325-33; and Frade R, et al., 2008 Cancer Gene Ther. 15:591-604) have caused tumor regression without seeming host toxicity. In addition, Duan et al. (Acta Otolyrngol 130: 25-30, 2010) demonstrated that local injection into the cochlea of lentiviral particles remained local without extension into the brain.

Both intratumoral injection of subcutaneous and possibly hepatic CRC xenografts as well as systemic injection of LV shRNA can be performed. shRNA to embryonic genes may be a useful therapy for liver metastases in CRC. First tumor implants in the livers of NOD/SCID mice are established, and then either intralesional or systemic treatment is performed with LV shRNA. The intralesional treatment of liver lesions cause LV pseudoparticles to be incorporated into the systemic circulation and require that mice with liver tumors will need appropriate, housing and husbandry as for direct systemic injection of LV pseudoparticles.

The lipid particles in which an active agent or therapeutic agent such as an interfering RNA (e.g., siRNA) is entrapped within the lipid portion of the particle and is protected from degradation, can be formed by any method known in the art including, but not limited to, a continuous mixing method, a direct dilution process, and an in-line dilution process.

In particular embodiments, the cationic lipids may comprise one or more of the cationic lipids described herein or salts thereof, alone or in combination with other cationic lipids. In other embodiments, the non-cationic lipids are egg sphingomyelin (ESM), distearoylphosphatidylcholine (DSPC), dioleoylphosphatidylcholine (DOPC), 1-palmitoyl2-oleoyl-phosphatidylcholine (POPC), dipalmitoyl-phosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (1-stearoyl-2-oleoyl-phosphatidylethanolamine (SOPS)), 16:0-18:1 PE (1-palmitoyl-2-oleoylphosphatidylethanolamine (POPE)), polyethylene glycol-based polymers (e.g., PEG 2000, PEG 5000, PEG-modified diacylglycerols, or PEG-modified dialkyloxypropyls), cholesterol, derivatives thereof, or combinations thereof.

Nucleic acid-lipid particles may be produced via a continuous mixing method, e.g., a process that includes providing an aqueous solution comprising a nucleic acid (e.g., interfering RNA) in a first reservoir, providing an organic lipid solution in a second reservoir (wherein the lipids present in the organic lipid solution are solubilized in an organic solvent, e.g., a lower alkanol such as ethanol), and mixing the aqueous solution with the organic lipid solution such that the organic lipid solution mixes with the aqueous solution so as to substantially instantaneously produce a lipid vesicle (e.g., liposome) encapsulating the nucleic acid within the lipid vesicle.

The action of continuously introducing lipid and buffer solutions into a mixing environment, such as in a mixing chamber, causes a continuous dilution of the lipid solution with the buffer solution, thereby producing a lipid vesicle substantially instantaneously upon mixing. The lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle The nucleic acid-lipid particles formed using the continuous mixing method typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

Nucleic acid-lipid particles may be produced via a direct dilution process that includes forming a lipid vesicle (e.g., liposome) solution and immediately and directly introducing the lipid vesicle solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of lipid vesicle solution introduced thereto. As a non-limiting example, a lipid vesicle solution in 45% ethanol when introduced into the collection vessel containing an equal volume of dilution buffer will advantageously yield smaller particles.

The nucleic acid-lipid particles formed using the direct dilution and in-line dilution processes typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein).

Once formed, the lipid particles are useful for the introduction of active agents or therapeutic agents (e.g., nucleic acids such as interfering RNA) into cells. Accordingly, the present invention also provides methods for introducing an active agent or therapeutic agent such as a nucleic acid (e.g., interfering RNA) into a cell. Preferably, the cell is a tumor cell such as, e.g., a cell present in a solid tumor. In certain embodiments, the cell may be a non-tumor cell that produces one or more angiogenic and/or growth factors associated with tumorigenesis or cell transformation. The methods are carried out in vitro or in vivo by first forming the particles as described above and then contacting the particles with the cells (e.g., cells of a solid tumor) for a period of time sufficient for delivery of the active agent or therapeutic agent to the cells to occur.

The lipid particles can be adsorbed to almost any cell type with which they are mixed or contacted. Once adsorbed, the particles can either be endocytosed by a portion of the cells, exchange lipids with cell membranes, or fuse with the cells. Transfer or incorporation of the active agent or therapeutic agent (e.g., nucleic acid) portion of the particle can take place via any one of these pathways. In particular, when fusion takes place, the particle membrane is integrated into the cell membrane and the contents of the particle combine with the intracellular fluid.

The lipid particles can be administered either alone or in a mixture with a pharmaceutically acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed.

A carrier includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically acceptable" refers to molecular entities and compositions that do not produce an allergic or similar untoward reaction when administered to a human.

The pharmaceutically acceptable carrier is generally added following lipid particle formation. Thus, after the lipid particle is formed, the particle can be diluted into pharmaceutically acceptable carriers such as normal buffered saline.

Systemic delivery for in vivo therapy, e.g., delivery of a therapeutic nucleic acid to a distal target cell via body systems such as the circulation, has been achieved using nucleic acid-lipid particles. For in vivo administration, administration can be in any manner known in the art, e.g., by injection, oral administration, inhalation (e.g., intransal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection. The lipid particles can be administered by direct injection at the site of disease or by injection at a site distal from the site of disease.

Where the lipid particles are administered intravenously, at least about 5%, 10%, 15%, 20%, or 25% of the total injected dose of the particles is present in plasma about 8, 12, 24, 36, or 48 hours after injection. In other embodiments, more than about 20%, 30%, 40% and as much as about 60%, 70% or 80% of the total injected dose of the lipid particles is present in plasma about 8, 12, 24, 36, or 48 hours after injection. In certain instances, more than about 10% of a plurality of the particles is present in the plasma of a mammal about 1 hour after administration. In certain other instances, the presence of the lipid particles is detectable at least about 1 hour after administration of the particle. In certain embodiments, the presence of a therapeutic agent such as a nucleic acid is detectable in cells of a tumor such as a solid tumor at about 8, 12, 24, 36, 48, 60, 72 or 96 hours after administration. In other embodiments, downregulation of expression of a target sequence by an interfering RNA (e.g., siRNA) is detectable at about 8, 12, 24, 36, 48, 60, 72 or 96 hours after administration. In yet other embodiments, downregulation of expression of a target sequence by an interfering RNA (e.g., siRNA) occurs preferentially in tumor cells. In further embodiments, the presence or effect of an interfering RNA (e.g., siRNA) in cells at a site proximal or distal to the site of administration or in cells of a tumor is detectable at about 12, 24, 48, 72, or 96 hours, or at about 6, 8, 10, 12, 14, 16, 18, 19, 20, 22, 24, 26, or 28 days after administration. In additional embodiments, the lipid particles are administered parenterally or intraperitoneally.

The compositions, either alone or in combination with other suitable components, can be made into aerosol formulations (i.e., they can be "nebulized") to be administered via inhalation (e.g., intranasally or intratracheally). Aerosol formulations can be placed into pressurized acceptable propellants, such as dichlorodifluoromethane, propane, nitrogen, and the like.

Vector Generation Considerations

The SBI LV shRNA particles are made in small research batches with kits obtained from SBI in the laboratory. Total yield is $10^{11}$ particles with a 1% TU rate. The shRNA particles are produced in research grade batches in 100 mm Petri dishes with total supernatants of less than 100 ml that are concentrated by high density ultracentrifugation and will have a 70% TU rate as expected from prior preparations. The total particle yield per lot is $10^{11}$ to $10^{12}$ vector particles. Lots are less than 10 ml for either preparation.

Methods of Using the Oligonucleotide or the Viral Vector for Treating Cancer

The compositions described above can be formulated into pharmaceutical compositions for treating a cancer. In every instance these compositions will comprise an oligonucleotide that is capable of inhibiting expression of NanogP8 while not interfering with expression of Nanog.

The efficacy of pharmaceutical compositions will be evaluated in terms of their ability to delivery the oligonucleotide to cancer cells.

Cancer cells of interest preferably include cancers derived from epithelial cells, more preferably gastric, colorectal (CRC), breast, glioblastoma, cervical cancers.

For pharmaceutical compositions comprising double stranded siRNA, a suitable lipid delivery system can be employed.

For pharmaceutical compositions comprising viral vector, the ability of the virus to infect cancer cells, more preferably colorectal cancer cells, can be measured. In either instance, the virus will contain an oligonucleotide comprising the sequences of SEQ ID NOS:3-44, more preferably selected from the group consisting of SEQ ID NOS: 3, 8, 34, and 37.

Methods of treating cancer in patients in need thereof using the pharmaceutical compositions described above are also readily demonstrated by those of skill in the art. These methods preferably include showing inhibition of cancer cells having a malignant phenotype, more preferably inhibiting cancer cells capable of metastasizing, also preferably inhibition of colorectal cancer cells.

EXAMPLES

Example 1

Spheroid Formation is Associated with Metastatic Potential

Figure 2:
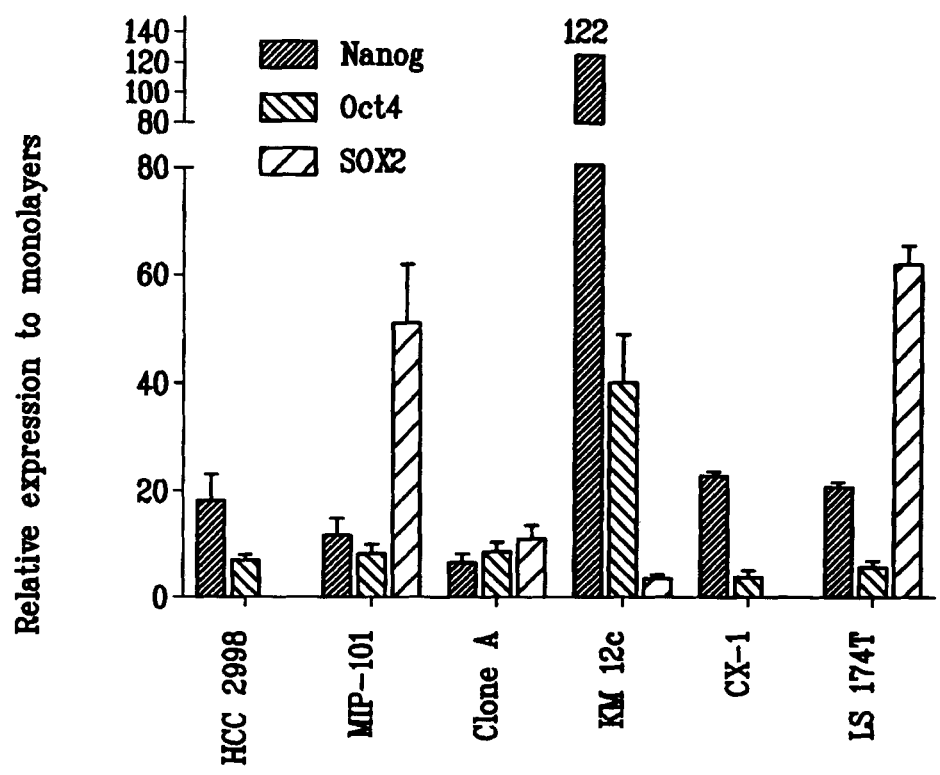
FIG. 2 shows relative expression of core embryonic genes in CRC spheroids and monolayer cultures. Total RNA isolated from seven day monolayer or spheroid cultures of CRC cell lines, including HCC2998, MIP-101, Clone A, CX-1 and LS174T. Expression levels of Nanog, POU5FI (OCT4), and SOX2 were measured by RT-PCR. E expression levels were normalized to the expression of GAPDH in each culture condition, and are shown in units of fold-change.

The ability of single CRC cells to form spheres, a hallmark of malignant potential, was tested in six cell lines in serum-free medium in ultra-low attachment plates in individual wells. Individual wells were scored to identify those with a single cell within the first 24 hr of plating. Spheroids that contained fifty or more cells were then scored in the single cell wells 7 to 14 days later. All CRC lines formed spheroids at frequencies that ranged from 1 to 56% of single cells plated (FIG. 2). The results for six human CRC lines are tabulated below and correlate with each line's malignant phenotype are summarized in Table 1.

TABLE 1

Characteristics of Human CRC lines

| Cell Line | Tumorigenicity | Metastatic Potential | Spherogenicity |
|---|---|---|---|
| HCC-2998 | + | 0% | 3% |
| Clone A | + | 5% | 12% |
| MIP-101 | + | 8% | 24% |
| KM-12c | + | 10% | 2% |
| CX-1 | + | 45% | 24% |
| LS 174T | + | 95% | 57% |

These results show that spherogenicity was associated with experimental metastatic potential. The formation of spheroids is a measure of the "sternness" of a CRC line in comparison to growth in monolayer culture, the basal condition for that cell line.

Example 2

Nanog Expression Increases During Spheroid Formation

Monolayer and spheroid cultures of these six cell lines were analyzed for the expression of embryonic stem cell transcription factors and CD44, CD133 or CD166 transcripts by qRT-PCR. Relative expression of Nanog transcripts was consistently increased in spheroids 10 to 20-fold compared to monolayer cultures except in KM12c while the relative expression of OCT4 was 10-fold and the SOX2 expression varied between 1 and 63-fold in spheroids compared to monolayer cultures. In contrast, the expression of CD44, CD133 or CD166 was not significantly increased in spheroid cultures compared to monolayer except in KM 12c, CX-1 and LS 174T. These results show that Nanog is activated as CRC transition to vertical growth to form spheroids. Nanog expression is consistently increased in all spheroid cultures compared to the companion monolayer culture. The expression of OCT4 is also increased in spheroids but generally less than Nanog while SOX2 expression is variable and sometimes much higher than Nanog or OCT4 expression. Another CRC line, KM-12c, expresses a 200-fold increase in Nanog but a 300-fold increase in SOX2 levels.

The results indicate that Nanog gene expression is consistently increased in spheroids compared to the expression in that line's monolayer culture while the expression of the other core embryonic genes OCT4 and SOX2 is more variable. These results suggest that Nanog may be a useful target for therapy.

Example 3

NanogP8 is the Dominant Form of Nanog Expressed in CRC Lines

To determine which Nanog gene product is expressed in human CRC required identifying a unique NanogP8 site around one of the 5 single nucleotide changes that is amenable to endonuclease digestion. A search of databases revealed that the only specific commercially available endonuclease that was predicted to cut NanogP8 cDNA but not Nanog was 143 nt 3' downstream to the ATG by AlwNI which cuts at the following sequence. The restriction endonuclease AlwNI identifies a palindromic hexanucleotide sequence in NanogP8 but not Nanog at position 144 relative to the translational start site.

Analyses of cDNA from the CRC lines by digestion with AlwNI show that NanogP8 is expressed in both the monolayer and spheroid cultures of the six CRC lines. The results were confirmed by direct sequencing of the cDNA.

NanogP8 was found to be more than 84% of the Nanog expressed in monolayer cultures of CX-1 and Clone A, and more than 94% of Nanog expressed in spheroids of these cells. On this basis, NanogP8 is the dominant form of Nanog expressed in CRC cell lines.

Example 4

NanogP8 is the Dominant Form of Nanog Expressed in Patient CRC

To determine whether Nanog and NanogP8 are expressed in CRC in patients, ten de-identified samples of colorectal carcinoma resected from patients treated at the NIH Clinical Center were analyzed for expression of Nanog and NanogP8 transcripts and protein. RT-PCR was followed by cutting the cDNA with the restriction endonuclease AlwNI that specifically cuts NanogP8 but not Nanog. Results of this analysis are presented in Table 2.

TABLE 2

Summary of results in liver samples

| | Total Ng+ | NP8+ | NP8 only | Ng only | Total Ng− | Total |
|---|---|---|---|---|---|---|
| Tumor | 8 | 6 | 2 | 1 | 2 | 10 |
| Adjacent normal | 4 | 1 | 0 | 3 | 6 | 10 |

The results indicate that Nanog transcripts are found in eight of ten tumor specimens and in four adjacent normal liver sections. Six of the eight tumor specimens contained NanogP8 transcripts. Two of the six specimens only contained NanogP8, four contained both Nanog and NanogP8 and one only Nanog. All results were confirmed by Sanger sequencing.

Based on these measurements, approximately 80% of clinical CRC metastases express a Nanog family member with 75% of those expressing NanogP8.

Example 5

NanogP8 Promoter Activity Increases During Spherogenicity

As shown above, levels of NanogP8 transcripts are increased in spheroids of the CRC cell lines Clone A and CX-1 cultured in SFM. The promoter activity of the NanogP8 gene was measured as CRC cells transition from a monolayer or two-dimensional culture to a spheroid or three-dimensional culture. The promoter activity of the NanogP8 gene was compared between monolayer and spheroid CRC cells. A lentiviral NanogP8 promoter GFP reporter was used to analyze cultures of CX-1 and Clone A. The results showed that monolayer cultures had low levels of GFP reporter expression compared to expression in spheroids of CX-1 and Clone A. In addition, the ubiquitous phosphoglycerate kinase (PGK) promoter was transduced into CX-1 and Clone A as a control, in which monolayer and spheroid transcriptional rates were found to be the same. In contrast, a 6- to 14-fold increase in GFP$^+$ cells was found in spheroids compared to monolayers for Clone A and CX-1. This is similar to the relative increase in transcripts assessed by qRT-PCR during transition from 2-D monolayers to 3-D suspension culture.

Accordingly, these results show that the increase in the levels of Nanog transcripts was due to increased Nanog promoter activity.

Example 6

NanogP8 is Expressed as a Protein in CRC Cells

To investigate if NanogP8 protein is expressed in CRC cells, the ten clinical samples of metastases and adjacent liver were stained with a commercially available Nanog antibody, which recognizes both Nanog and NanogP8. Analysis of the immunofluorescent antibody (IFA) staining indicates that staining is cytoplasmic in CRC and present only in tumors or adjacent liver that contained Nanog or NanogP8 transcripts. In contrast, a control specimen of a human germ cell tumor has the expected intranuclear location for Nanog.

To identify the NanogP8 protein directly in CRC cell lines, tandem MS/MS was used. Extracts of CRC cell lines were immunoprecipitated, isolated by SDS-PAGE, subjected to in gel tryptic digestion and then MS/MS. Four Nanog-related peptides (KTWFQNQRM, KYLSLQQMQELSNILNL-SYKQ, KKEDKVPVKK, and KGKQPTSAENSVAKK) were identified in extracts from Clone A overexpressing NanogP8. The last peptide is unique to NanogP8, which includes the shift from Lys (K) in Nanog to Asn (N) in NanogP8 at codon 82. This amino acid change was confirmed by gene sequencing. Nanog/NanogP8 proteins were not identified in extracts of CRC cell lines without overexpression by transduction presumably because CRC cell lines express low levels of endogenous proteins.

Example 7

Allele-Specific shRNA-Mediated Inhibition of NanogP8

Several fatal neurodegenerative human diseases are caused by single nucleotide polymorphisms (SNPs) that cause mutant proteins to be formed through alternative splicing as well as insertion of CAG-repeats into critical structural proteins. Thus, neuroscientists have developed strategies for designing inhibitory RNAs that preserve the function of the wild type protein but inhibit the expression of mutant genes that often differ by a single SNP. Using principles derived from these studies (Huang, et al. 2009, Nucl Acids Res 37:7560-69; and Dykxhoorn, et al. 2006, PNAS 103:5953-58), a series of allele-specific shRNAs that target NanogP8 expression have been designed by us and are here partly evaluated both for specificity of inhibition as well as inhibition of spherogenicity. Allele-specific inhibitory shRNAs described herein are driven by the H1 promoter and contain a CMV driven GFP fluorescent protein that can be used as a reporter in Lentiviral vectors from Systems Biosciences, Inc (SBI). These structures are labeled either NanogP8- or Ng- for shRNAs that target either NanogP8 or Nanog respectively. For comparison the commercially available shRNAs from Sigma are also shown that were based on the original designs by members of the RNAi Consortium that is led by investigators primarily from the Broad Institute using their design algorithm.

The shRNAs used to target Nanog or NanogP8 are listed in Table 3, below. The commercially available shRNAs designated by the prefix TRCN (Sigma-Aldrich) contain shRNA driven by a U6 promoter as well as a puromycin resistance element driven by a CMV promoter. The Np8-, Ng- or Control (CONT) lentivectors shRNA expression vectors of SEQ ID NOS: 1-44 are pPS-H1-LCS-GFP and pPS-H1-LCS-RFP; and overexpression vector is pPS-EF1-LCS-T2A-RFP (System Biosciences, Inc.). Packaging plasmids from the Lab of Experimental Carcinogenesis: pVSV-G and pPACK-GAG/REV. HEK293TN cells were used for packaging according to the protocol from SBI. Asterisk* denotes the lenti viral particle that was used to construct shNanog transduced CRC. shOCT4 and shSOX2 were selected from a commercial source (Sigma). Both the SBI and Sigma lentiviruses are HIV-based lentiviruses that produce replication deficient pseudoparticles.

TABLE 3

Allele-Specific Inhibitory shRNAs to Nanog

| Name/Cat # | Sequence | SEQ ID NO: |
|---|---|---|
| NP8-1-1 | GAGGCAGCAGAGACCGCTGCATGCACTTCCAGCCA | 3 |
| NP8-1-2 | TCTGACAGGAAGTGGCTGGAAGTGCATGCAG | 4 |
| NP8-1-3 | CTTCCTGTCAGATGGCTGGAAGTGCATGCAGTTTTT | 5 |
| NP8-1-4 | CGAACAGAGAGAGACCGAAAAACTGCATGCACTTCCAGCCA | 6 |
| NP8-2-1 | GAGGCAGCAGAGACCGCTGCATGCACTTCCAGCCG | 7 |
| NP8-2-2 | TCTGACAGGAAGTGGCTGGAAGTGCATGCAG | 8 |
| NP8-2-3 | CTTCCTGTCAGATGGCTGGAAGTGCATGCAGTTTTT | 9 |
| NP8-2-4 | CGAACAGAGAGAGACCGAAAAACTGCATGCACTTCCAGCCG | 10 |
| NP8-3-1 | GAGGCAGCAGAGACCGTTGTGATCCGCCCGCCTCG | 11 |
| NP8-3-2 | TCTGACAGGAAGCGAGGCGGGCGGATCACAA | 12 |
| NP8-3-3 | CTTCCTGTCAGACGAGGCGGGCGGATCACAATTTTT | 13 |
| NP8-3-4 | CGAACAGAGAGAGACCGAAAAATTGTGATCCGCCCGCCTCG | 14 |
| NP8-4-1 | GAGGCAGCAGAGACCGATCTAATACGAGTTTGGATA | 15 |
| NP8-4-2 | TCTGACAGGAAGTATCCAAACTCGTATTAGAT | 16 |
| NP8-4-3 | CTTCCTGTCAGATATCCAAACTCGTATTAGAT TTTTT | 17 |
| NP8-4-4 | CGAACAGAGAGAGACCGAAAAAATCTAATACGAGTTTGGATA | 18 |
| NP8-5-1 | GAGGCAGCAGAGACCGATCTAATACGAGTTTGGATG | 19 |

TABLE 3-continued

Allele-Specific Inhibitory shRNAs to Nanog

| Name/Cat # | Sequence | SEQ ID NO: |
|---|---|---|
| NP8-5-4 | CGAACAGAGAGAGACCGAAAAAATCTAATACGAGTTTGGATG | 20 |
| NP8-6-1 | GAGGCAGCAGAGACCGATGAGTACTACTTTAGTTG | 21 |
| NP8-6-2 | TCTGACAGGAAGCAACTAAAGTAGTACTCAT | 22 |
| NP8-6-3 | CTTCCTGTCAGACAACTAAAGTAGTACTCATTTTTT | 23 |
| NP8-6-4 | CGAACAGAGAGAGACCGAAAAAATGAGTACTACTTTAGTTG | 24 |
| NP8-7-1 | GAGGCAGCAGAGACCGAACAAAGCACATCTTGCCAGGA | 25 |
| NP8-7-2 | TCTGACAGGAAGTCCTGGCAAGATGTGCTTTGTT | 26 |
| NP8-7-3 | CTTCCTGTCAGATCCTGGCAAGATGTGCTTTGTTTTTT | 27 |
| NP8-7-4 | CGAACAGAGAGAGACCGAAAAAACAAAGCACATCTTGCCAGGA | 28 |
| NP8-8-1 | GAGGCAGCAGAGACCGAACAAAGCACATCTTGCCAGGG | 29 |
| NP8-8-2 | TCTGACAGGAAGTCCTGGCAAGATGTGCTTTGTT | 30 |
| NP8-8-3 | CTTCCTGTCAGATCCTGGCAAGATGTGCTTTGTTTTTT | 31 |
| NP8-8-4 | CGAACAGAGAGAGACCGAAAAAAACAAAGCACATCTTGCCAGGG | 32 |
| Ng-1-1 | GAGGCAGCAGAGACCGCTGCATGCAGTTCCAGCCA | 33 |
| Ng-1-2 | TCTGACAGGAAGTGGCTGGAACTGCATGCAG | 34 |
| Ng-1-3 | CTTCCTGTCAGATGGCTGGAACTGCATGCAGTTTTT | 35 |
| Ng-1-4 | CGAACAGAGAGAGACCGAAAAACTGCATGCAGTTCCAGCCA | 36 |
| Ng2-1 | GAGGCAGCAGAGACCGCTGCATGCAGTTCCAGCCG | 37 |
| Ng2-2 | TCTGACAGGAAGTGGCTGGAACTGCATGCAG | 38 |
| Ng2-3 | CTTCCTGTCAGATGGCTGGAACTGCATGCAGTTTTT | 39 |
| Ng2-4 | CGAACAGAGAGAGACCGAAAAACTGCATGCAGTTCCAGCCG | 40 |
| Cont-1 | GAGGCAGCAGAGACCGTAGCGACTAAACACATCAA | 41 |
| Cont-2 | TCTGACAGGAAGTTGATGTGTTTAGTCGCTA | 42 |
| Cont-3 | CTTCCTGTCAGATTGATGTGTTTAGTCGCTATTTTT | 43 |
| Cont-4 | CGAACAGAGAGAGACCGAAAAATAGCGACTAAACACATCAA | 44 |
| TRCN004884 | CCGGGCTGCTAAGGACAACATTGATCTCGAGATCAATGTTGTCCTTAGCAGCTTTTT | 45 |
| TRCN004885* | CCGGGCTTTGAAGCATCCGACTGTACTCGAGTACAGTCGGATGCTTCAAAGCTTTTT | 46 |
| TRCN004886 | CCGGCTGTAAAGAATCTTCACCTATCTCGAGATAGGTGAAGATTCTTTACAGTTTTT | 47 |
| TRCN004887 | CCGGCCTGGAACAGTCCCTTCTATACTCGAGTATAGAAGGGACTGTTCCAGGTTTTT | 48 |
| TRCN004888 | CCGGCCTAAACTACTCCATGAACATCTCGAGATGTTCATGGAGTAGTTTAGGTTTTT | 49 |

Double stranded siRNA effective in selectively knocking down Nanog parent gene expression include the following sequences.

Ng-siRNA-1:
Sense:
SEQ ID NO: 50
5'-CTGCATGCAGTTCCAGCCA-3'
Antisense:
SEQ ID NO: 51
5'-TGGCTGGAACTGCATGCAG-3'

Ng-siRNA-2:
Sense:
SEQ ID NO: 52
5'-CTGCATGCAGTTCCAGCCG-3'
Antisense:
SEQ ID NO: 53
5'-TGGCTGGAACTGCATGCAG-3'

Double stranded siRNA effective in selectively knocking down NanogP8 pseudogene expression include the following sequences.

```
NP8-siRNA-1:
Sense:
                                       SEQ ID NO: 54
5'-CTGCATGCACTTCCAGCCA-3'
Antisense:
                                       SEQ ID NO: 55
5'-TGGCTGGAAGTGCATGCAG-3'

NP8-siRNA-2:
Sense:
                                       SEQ ID NO: 56
5'-CTGCATGCACTTCCAGCCG-3'
Antisense:
                                       SEQ ID NO: 57
5'-TGGCTGGAAGTGCATGCAG-3'
```

Transduction with the herein described allele-specific shRNAs of both monolayer cultures as well as cells in suspension has been achieved with 50 to 90% efficiency as defined by GFP fluorescence.

Example 7

Modulating Nanog Expression Changes Spherogenicity of CRC Cells

If therapy to inhibit Nanog expression by lentiviral-delivered shRNA is to be successful, then it is important to demonstrate that Nanog shRNA can be delivered to cells in 3-D colonies. The main CRC lines growing in suspension can readily be transduced by the vectors described herein.

Screening of constructs shows that Np8-1-1 is an active candidate since it inhibits the spheroid formation of CX-1, Clone A and LS 174T cells (Table 4).

TABLE 4

Summary of Single Cell Spherogenicity Assays

| Cell Line | Construct | Spheroid | Single Cell/Cluster | % | P |
|---|---|---|---|---|---|
| CX-1 | shNanog | 10 | 120 | 8 | 0.004 |
| | pLKO.1 | 31 | 72 | 30 | NS |
| | Ng-1-2 | 13 | 10 | 57 | 0.04 |
| | Np8-2-2 | 12 | 20 | 38 | NS |
| | Ng-2-1 | 1 | 88 | 1 | <0.001 |
| | Np8-1-1 | 1 | 99 | 1 | <0.001 |
| | Parental | 24 | 77 | 24 | — |
| LS 174T | shNanog | 12 | 32 | 27 | 0.0031 |
| | pLKO.1 | 15 | 15 | 50 | NS |
| | Ng-1-2 | 9 | 28 | 24 | 0.02 |
| | Np8-2-2 | 13 | 20 | 39 | NS |
| | Ng-2-1 | 1 | 31 | 3 | <0.001 |
| | Np8-1-1 | 1 | 65 | 2 | <0.001 |
| | Parental | 37 | 28 | 57 | — |
| Clone A | shNanog | 1 | 139 | 0.7 | 0.0003 |
| | pLKO.1 | 5 | 79 | 6 | NS |
| | Ng-1-2 | 11 | 9 | 55 | 0.001 |
| | Np8-2-2 | 10 | 12 | 45 | 0.008 |
| | Ng-2-1 | 0 | 47 | 0 | 0.06 |
| | Np8-1-1 | 0 | 56 | 0 | 0.026 |
| | Parental | 9 | 64 | 12 | — |

CRC cells were plated at 0.6 cells/well in serum-free medium. Wells were scored within 24 hours for single cells. All wells containing a single cell were then re-evaluated at least 9 days after plating for formation of spheroids (≥50 cells in a compact spherical assembly). Spheroid is the number of single cells that formed spheroids; Single Cell/Cluster is the number of single cells that did not form spheroids. P value is calculated by Fisher S exact test corrected for multiple comparisons by Bonferroni correction. Each shRNA has been tested in at least two separate assays except for the Clone A Ng-1-2 and Np8-2-2 lentivectors. NP8 shRNA does not inhibit Nanog gene expression significantly in a human cell line that expresses Nanog without NanogP8. NanogP8-1 (Np8-1-1) causes a ~50% decrease in Nanog levels in CX-1 cells but no significant decrease in levels in PA-1 cells.

Allele-specific inhibitory shRNA inhibit the expression of its specific target but not that of either the wild type, parental, or a gene which is Nanog. As shown below, Np8-1-1 inhibits the expression of Nanog by RT-PCR in CX-1 cells that produce a preponderance of NanogP8. However, Np8-1-1 does not inhibit expression of parental Nanog by RT-PCR in human PA-1 embryonic carcinoma cells that produce only parental Nanog and no other pseudogenes whose mRNA might be amplified. This confirms that Np8-1-1 is an allele-specific inhibitor.

Whole transcriptome analyses of CX-1 and Clone A in monolayer and spheroid culture shows that NanogP8 has at most 200 reads even in spheroids, Nanog may have less than 10 in transcriptomes that contain 10-40 million reads. As a result, a gene therapy approach to targeting NanogP8 will block the progression of CRC once it has metastasized. While these results identify a promising lead candidate to inhibit CX-1 and possibly reduce the growth of the more aggressive LS 174T, other candidates may be more active and/or specific. Inhibition of this low abundance gene will have profound effects in decreasing metastatic potential by both inhibiting cell proliferation and inducing apoptosis.

Figure 3:
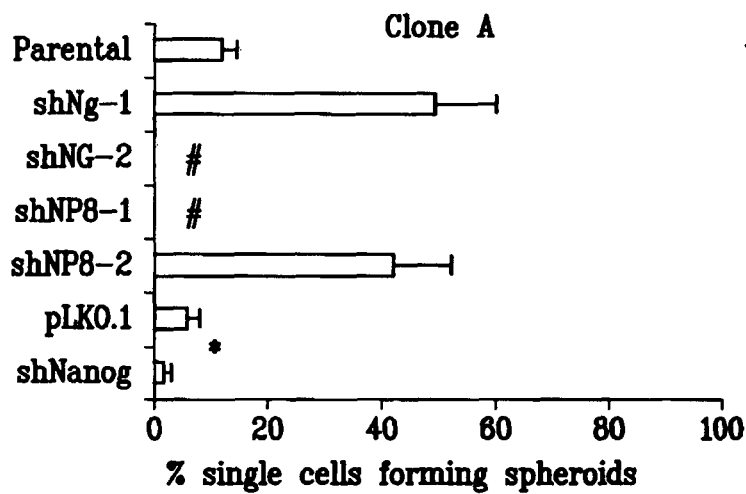
FIG. 3 shows specific inhibition of NanogP8 and NanogP8 affects side population in CRC Cells. Fig Effect of shRNA on single cell spherogenicity of Clone A, CX-1, and LS 174T. shNP8-1 and shNg-2 are more active than the commercially available shNanog against all 3 human CRC. Mean %±SD. P values by contingency table analysis with Bonferroni correction. P values after Bonferroni correction of contingency table analysis. # $P<0.001$ vs Parental CRC. * $P<0.01$ vs Parental CRC.
Figure 3:
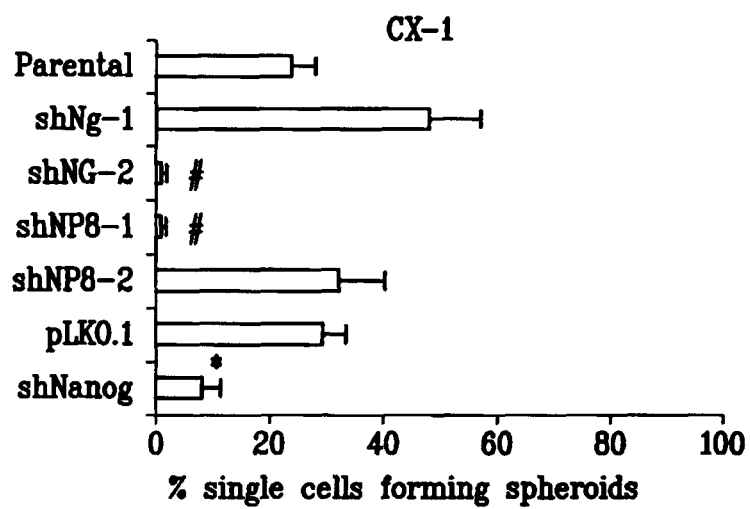
Figure 3:
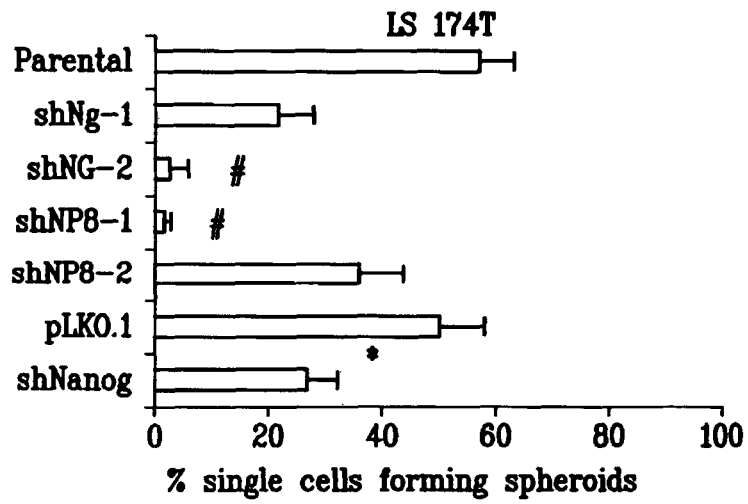

Total Nanog mRNA expression was inhibited using lentiviral-delivered shRNA technology to examine the functional relevance of Nanog in spherogenicity in CRC cell lines. The efficiency of shRNA targeting of Nanog was confirmed by RT-PCR assay and immunoblotting. Spherogenicity was measured by plating single CRC cells in serum-free medium and then scoring spheroids of fifty or more cells after at least nine days of culture. Inhibiting Nanog transcripts significantly inhibited formation of spheres in both Clone A and CX-1 by 40% to 90% compared to untreated parental cells and cells transduced with the empty vector pLKO.1. A 50% inhibition was also observed in LS 174T cells transduced with shNanog. The data indicate that inhibition of Nanog consistently inhibits spherogenicity in the three CRC lines (FIG. 3). Single cell spherogenicity, tumorigenicity and in one CRC line metastatic potential have been assessed.

Inhibition of Nanog by shRNA consistently inhibits spherogenicity in each CRC line while shRNA to SOX2 and OCT4 also significantly inhibits the spherogenicity of LS 174T. However, inhibition of either OCT4 or SOX2 increases the spherogenicity of Clone A and CX-1. Also Nanog appears to be the dominant gene because in CX-1 and Clone A inhibition of Nanog inhibits SOX2 and OCT4 but not vice versa. This is consistent with the function of these genes in early implantation embryos. Nanog may inhibit tumor growth through direct inhibition of WEE1 gene and phosphorylation of WEE1 and cdc2$^{P34}$ (CDKN1). Alternatively, Nanog may decrease resistance to apoptosis by inhibiting anti-apoptotic genes such as BCL-2 and MLL in CRC.

In both Clone A and CX-1 cells, when Nanog or NanogP8 are overexpressed there is an increase in the formation of spheroids from single cells compared to parental untreated cells. This is ~12% for Clone A and about 23-25% for CX-1. This is in contrast to results above that show that spherogenicity is decreased by inhibiting Nanog. Thus, spherogenicity is inhibited by inhibiting Nanog and increase by increasing Nanog or NanogP8. In every instance, results are based on a single cell spherogenicity assay in serum free medium in which each well is scored for the presence of a single cell, and spheroids are separately assessed 9+ days later. Spheroids are defined as cell masses of fifty or more cells.

In contrast, when Clone A and CX-1 cells were transduced with lentiviral vectors expressing full length Nanog, the increased Nanog expression increased spherogenicity in Clone A by about 9-fold compared to untreated or vector controls but not in CX-1.

Taken together, these results show that inhibition of Nanog gene expression inhibits growth of human CRC xenografts in vivo. These results indicate that Nanog expression has an important role in the capacity of single CRC cells to form spheroids and also indicates that the suspension cultures in serum-free medium may promote the enrichment of tumor-initiating cells with characteristics of sternness.

Example 8

Inhibition of 3-D Growth by Transduction Nanog/NanogP8 shRNA

It was important to determine how the LV shRNA modulates apoptosis in 3-D culture. Anoikis—apoptosis caused by suspension culture—is dependent on activation of Caspase 8. Caspase 3, 8 and 9 activity was measured in Clone A and CX-1 treated with LV shRNA at 4 days of suspension culture, 3 days after LV treatment. shRNA to Nanog and NanogP8 caused an increase in the activity of Caspase 3 in both CX-1 and Clone A cells. shRNA Np8-1 also increased the activity of Caspase 8 or 9 in Clone A or CX-1, respectively. Cells that were adjacent to transduced cells but not expressing the MD also had similar levels of Caspase 9 activity, pointing to an effect of transduced cells on neighbors. The results confirm that Caspase 9 and the intrinsic pathway that uses mitochondrial amplification in apoptosis is important for apoptosis mediated by shNp8-1 and shNG-1. shRNA to NanogP8 and Nanog induced apoptosis and 3-D growth by the activation of the intrinsic pathway. This is distinct from the mechanism of apoptosis in these cells induced by anoikis which depends solely on the extrinsic pathway of apoptosis.

Example 9

Inhibition of Nanog Inhibits Tumorigenicity and Metastasis

Figure 4:
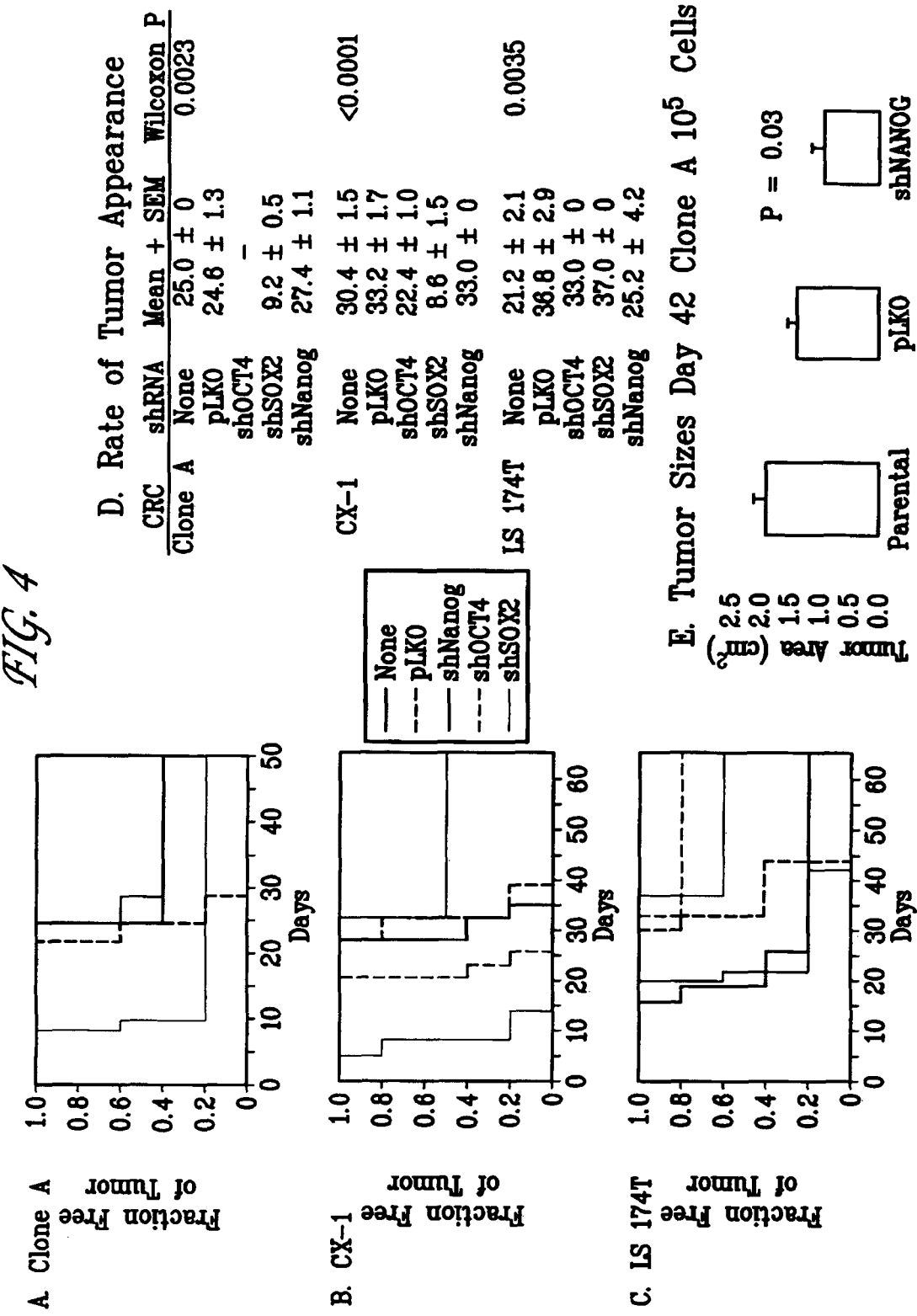
FIG. 4 shows the effect of inhibiting core embryonic genes on growth of CRC cell lines. Groups of 5-15 NOD/SCID mice were injected SC with $10^5$ viable cells in PBS that had been stably transduced with lentiviral shRNA to Nanog, OCT4, or SOX2 with the empty vector pLKO and the untreated parental control (None) as controls for Clone A (A), CX-1 (B) and LS 174T (C). Kaplan-Meier plots present data for time to tumor appearance with Mean±SEM days presented in Panel D. Probability is the Wilcoxon log rank significance level for each tumor group in Panels A-C. In Panel E, the one way analysis of variance is presented for those Clone A tumors 42 days after tumor injection in the None (Parental), pLKO or shNanog groups.

CRC were injected subcutaneously in NOD/SCID mice in cell dilutions of $10^3$-$10^5$ cells per mouse. At $10^3$ and $10^4$ cells per mouse CX-1 cells transduced with shNanog that inhibits both Nanog and NanogP8 expression had fewer tumors than did either the parental cell line or the pLKO.1 empty vector control. In contrast, the shNanog-transduced Clone A cells were less tumorigenic than the pLKO.1 control but were similar to the tumor growth rates in the parental Clone A cells that are more weakly tumorigenic than CX-1 cells (FIG. 4). Different constructs were tested in NOD/SCID mice by subcutaneous injection of $10^5$ cells to assess tumorigenicity at a consistent cell concentration between experiments. The results showed that growth of shNanog transduced CX-1 and Clone A cells was slower than the pLKO.1 control since the median number of days to palpable tumor is increased by 16% for Clone A and not reached for CX-1 (Tables 5 and 6; and FIG. 7).

TABLE 5

| | Median (days) | |
|---|---|---|
| | Clone A | CX-1 |
| pLKO.1 | 25 | 33 |
| shNanog | 29 | >50 |
| Nanog | 23 | 18 |

TABLE 6

| | % Tumor free | |
|---|---|---|
| | Clone A | CX-1 |
| pLKO.1 | 0 | 0 |
| shNanog | 40 | 50 |
| Nanog | 0 | 0 |

In addition, 40% of the mice in the shNanog Clone A groups remained tumor free during the time of the experiment. Thus, shNanog decreased growth of CX-1 but had minor effects on Clone A.

Figure 5:
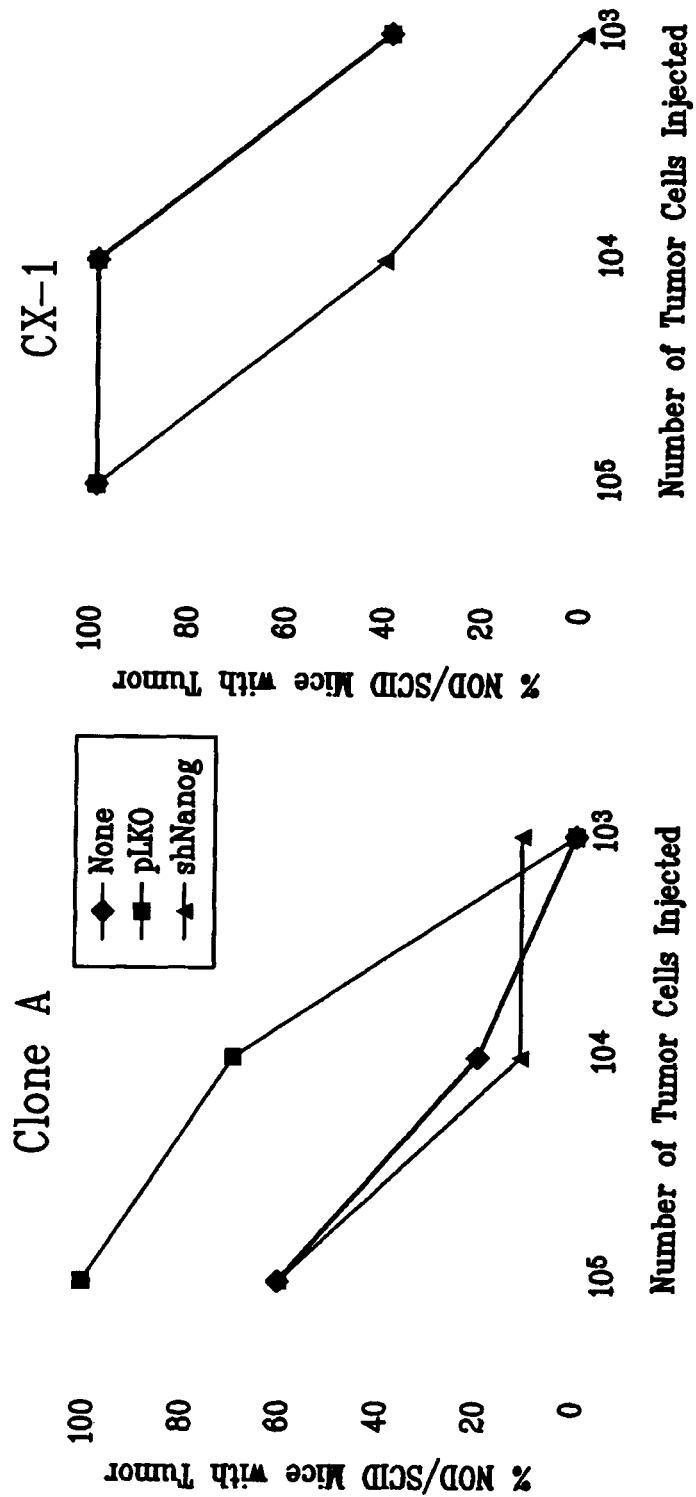
FIG. 5 shows shNanog inhibits single cell tumorigenicity. Groups of 5-10 NOD/SCID mice were injected with dilutions of $10^5$-$10^3$ viable CX-1 or Clone A cells subcutaneously in NOD/SCID mice. Parental, pLKO.1 and shNanog transductants were scored for the appearance of tumors over 70 days after tumor inoculation.
Figure 6:
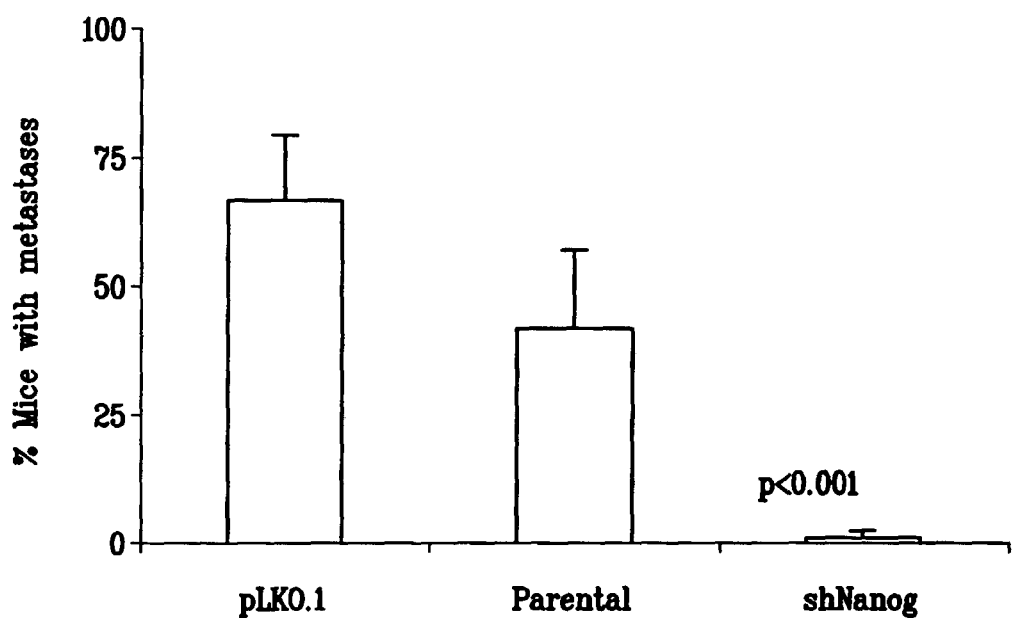
FIG. 6 shows shNanog inhibits experimental metastasis. When $2\times10^6$ CX-1 cells were injected into the spleens of NOD/SCID mice, no shNanog transduced CX-1 cells formed either gross or microscopic liver experimental metastases whereas 45 to 70% of mice injected with parental or control vector did. Error bars: SD; * $P<0.01$ vs Parental CRC. P value by contingency table analysis with Bonferroni correction. Experimental metastasis from Parental CX-1 did not generate fibrosis or host inflammatory response.

Another test of the effect of shRNA to Nanog on the malignant phenotype involves experimental metastasis since liver colonization after intrasplenic injection of viable CRC cells is associated with recurrence in patients operated on for cure. shNanog transduced CX-1 cells failed to form grossly visible or microscopic hepatic liver colonies compared to either the untreated parental CX-1 cells or CX-1 cells transduced with the control vector pLKO.1 (FIG. 5). These results suggest that inhibition of Nanog function may be important to preventing progression of CRC.

Clone A is less tumorigenic than CX-1 and shNanog does not decrease the rate of tumor takes compared to the parental line although shNanog developed fewer tumors than the vector control. However, shNanog significantly slowed the rate of growth of Clone A tumors compared to either the vector control or the parental line (FIG. 4E). While shSOX2 stimulated the appearance of Clone A tumors, shOCT4 delayed the appearance tumors of Clone A. shNanog in CX-1 inhibits tumor growth in both the parental and the vector control, whereas both shOCT4 and shSOX2 shorten the time to appearance of tumors in CX-1 (FIG. 4B). LS 175T is considerably more tumorigenic than Clone A or CX-1 since the parental cell line has a shorter mean time to appearance (21.2 days) than Clone A (25 days) and CX-1 (30.4 days). shNanog does not inhibit tumor appearance compared to the parental line or vector control. In contrast to their activity in the other CRC, both shOCT4 and shSOX2 inhibited the formation of LS 174T tumors in shSOX2 (FIGS. 4C and 4D). The results indicate that shNanog significantly decreases the rate of growth of tumors compared to the vector control or the parental cell line.

Example 10

Nanog Inhibition Blocks Metastasis of CRC Cells

Figure 7A:
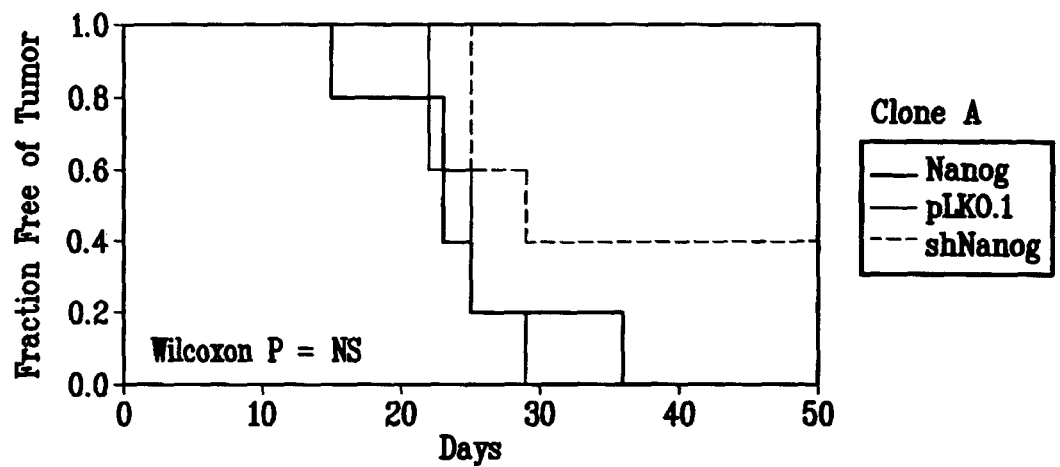
FIG. 7 shows shNanog inhibits tumorigenicity. Clone A or CX-1 cells were transduced with the pLKO.1 (green), shNanog (orange), or Nanog (blue). shNanog decreases growth by prolonging the median days to appearance of tumors for both Clone A and CX-1 as well as the percentage of mice that are tumor free in mice injected with CX-1 cells. Overexpression of Nanog and NanogP8 shortened the median number of days to tumor appearance in CX-1 compared to the pLKO.1.
Figure 7B:
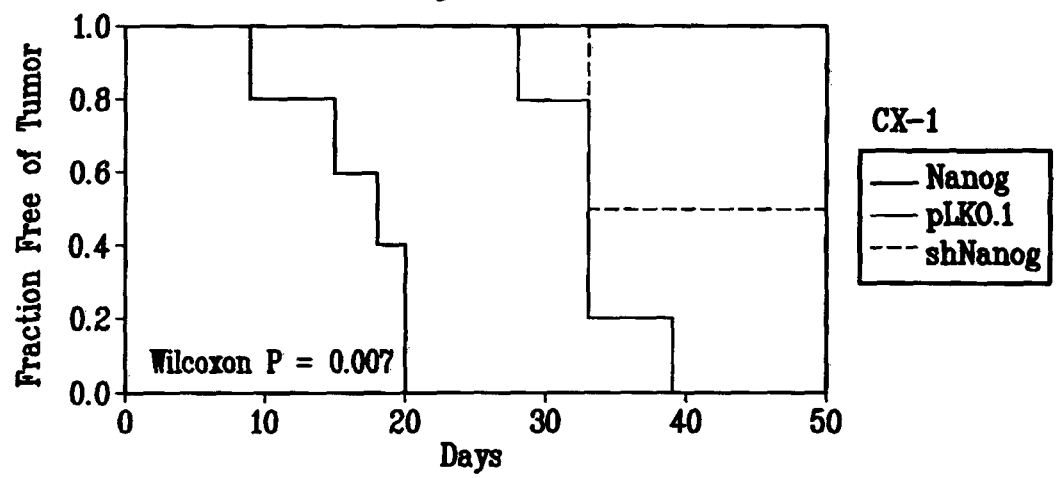

One aspect of this description is a therapy to effectively inhibit the formation of liver metastases in patients with CRC. Recurrence in patients operated upon for cure is associated strongly with the ability of their freshly isolated CRC to form liver colonies after intrasplenic injection. Clone A forms too few liver colonies after intrasplenic injection to study. In contrast, NOD/SCID mice receiving shNanog transduced CX-1 did not develop microscopic or grossly visible liver colonies compared to mice that received CX-1 cells that were either untreated parental cells or cells transduced with the empty vector pLKO (FIG. 7).

These data suggest that targeting Nanog and perhaps OCT4 or SOX2 in appropriate CRC may inhibit growth of CRC even at common sites of metastases. Treatment might be tailored to individual CRC by typing the ratio of Nanog, SOX2 and OCT4 in the spheroid-forming cells within a CRC. A lentiviral vector was found to be effective as a potential gene therapy to deliver shRNA encoding Nanog. This RNA consistently inhibits tumor growth in vitro, increased the time to tumor appearance in 2 of 3 CRC lines and blocked experimental metastasis in a moderately aggressive CRC.

The scope of description is not limited to the examples provided above, and is hereby supplemented by the skill of the ordinary artisan. All publications cited above are hereby incorporated by such reference in their entirety into the description of this specification. The contents of all publications cited above are incorporated herein in their entirety

What is claimed:

1. An inhibitory RNA molecule, comprising an oligonucleotide that knocks down expression of either Nanog or NanogP8 wherein the oligonucleotide comprises a sequence of SEQ ID NO:3 (5'-GAGGCAGCAGAGACCGCTGCATG-CACTTCCAGCCA-3') or SEQ ID NO:37 (5'-GAGGCAG-CAGAGACCGCTGCATGCAGTTCCAGCCG-3').

2. The inhibitory RNA molecule of claim 1, wherein the oligonucleotide knocks down expression of Nanog.

3. The inhibitory RNA molecule of claim 1, wherein the oligonucleotide knocks down expression of NanogP8.

4. A viral vector, comprising the inhibitory RNA molecule according to claim 1.

5. The viral vector of claim 4, wherein the vector is capable of inducing apoptosis of cancer cells.

6. The viral vector of claim 4, wherein the vector is capable of inhibiting cancer cell proliferation.

7. The viral vector of claim 4, wherein the vector is capable of inhibiting tumor mass.

8. The viral vector of claim 4, wherein the viral vector is packaged in a coat protein that specifically binds to colorectal carcinoma (CRC) cells.

9. The viral vector of claim 4, wherein the viral vector is capable of overexpressing an RNA that inhibits either NanogP8 or Nanog expression.

10. A pharmaceutical composition, comprising the vector according to claim 4.

11. A pharmaceutical composition, comprising the inhibitory RNA molecule according to claim 1.

12. A pharmaceutical composition comprising a viral vector, wherein the viral vector is capable of producing the inhibitory RNA molecule according to claim 1.

13. The pharmaceutical composition of claim 12, wherein the inhibitory RNA molecule is a double stranded siRNA.

14. An inhibitory RNA molecule, comprising an oligonucleotide that knocks down expression of either Nanog or NanogP8 wherein the oligonucleotide has a sequence of SEQ ID NO:8 (5'-TCTGACAGGAAGTGGCTGGAAGTGCAT-GCAG-3') or SEQ ID NO:34 (5'-TCTGACAGGAAGTG-GCTGGAACTGCATGCAG-3').

15. The inhibitory RNA molecule of claim 14, wherein the oligonucleotide knocks down expression of Nanog.

16. The inhibitory RNA molecule of claim 14, wherein the oligonucleotide knocks down expression of NanogP8.

17. A viral vector, comprising the inhibitory RNA molecule according to claim 14.

18. The viral vector of claim 17, wherein the vector is capable of inducing apoptosis of cancer cells.

19. The viral vector of claim 17, wherein the vector is capable of inhibiting cancer cell proliferation.

20. The viral vector of claim 17, wherein the vector is capable of inhibiting tumor mass.

21. The viral vector of claim 17, wherein the viral vector is capable of overexpressing an RNA that inhibits either NanogP8 or Nanog expression.

22. A pharmaceutical composition, comprising the vector according to claim 17.

23. A pharmaceutical composition, comprising the inhibitory RNA molecule according to claim 14.

24. A pharmaceutical composition, comprising a viral vector, wherein the viral vector is capable of producing the inhibitory RNA molecule according to claim 14.

* * * * *